(12) United States Patent
Ella et al.

(10) Patent No.: US 10,058,605 B2
(45) Date of Patent: Aug. 28, 2018

(54) VACCINE COMBINATIONS

(71) Applicant: Bharat Biotech International Limited, Hyderabad (IN)

(72) Inventors: Krishna Murthy Ella, Hyderabad (IN); Kandaswamy Sumathy, Hyderabad (IN)

(73) Assignee: Bharat Biotech International Limited, Hyderabad (IN)

( * ) Notice: Subject to any disclaimer, the term of this patent is extended or adjusted under 35 U.S.C. 154(b) by 0 days.

(21) Appl. No.: 14/399,147

(22) PCT Filed: May 9, 2013

(86) PCT No.: PCT/IN2013/000306
§ 371 (c)(1),
(2) Date: Nov. 5, 2014

(87) PCT Pub. No.: WO2013/168182
PCT Pub. Date: Nov. 14, 2013

(65) Prior Publication Data
US 2016/0015804 A1     Jan. 21, 2016

(30) Foreign Application Priority Data

May 9, 2012 (IN) .............................. 486/CHE/2012

(51) Int. Cl.
| | | |
|---|---|---|
| *A61K 39/29* | (2006.01) | |
| *A61K 39/00* | (2006.01) | |
| *A61K 39/12* | (2006.01) | |
| *C12N 7/00* | (2006.01) | |

(52) U.S. Cl.
CPC ........ *A61K 39/292* (2013.01); *A61K 39/0016* (2013.01); *A61K 39/0018* (2013.01); *A61K 39/12* (2013.01); *A61K 39/29* (2013.01); *C12N 7/00* (2013.01); *A61K 2039/5258* (2013.01); *A61K 2039/54* (2013.01); *A61K 2039/545* (2013.01); *A61K 2039/55505* (2013.01); *A61K 2039/55583* (2013.01); *A61K 2039/70* (2013.01); *C12N 2710/20022* (2013.01); *C12N 2710/20034* (2013.01); *C12N 2710/20052* (2013.01); *C12N 2730/10022* (2013.01); *C12N 2730/10034* (2013.01); *C12N 2730/10052* (2013.01); *C12N 2730/10122* (2013.01); *C12N 2730/10134* (2013.01); *C12N 2730/10152* (2013.01); *C12N 2770/28134* (2013.01)

(58) Field of Classification Search
None
See application file for complete search history.

(56) References Cited

FOREIGN PATENT DOCUMENTS

WO    WO2010001409 A2 *   1/2010

OTHER PUBLICATIONS

Combelas et al. Papillomavirus pseudovirions packaged with the L2 gene induce cross-neutralizing antibodies. Journal of Translational Medicine 2010, 8:28.*
Barreto et al. Humoral immunity 5 years after booster immunization with an adolescent and adult formulation combined tetanus, diphtheria, and 5-component acellular pertussis vaccine. Vaccine. Nov. 23, 2007;25(48):8172-9. Epub Oct. 2, 2007.*
Barreto et al. Humoral immunity 5 years after booster immunization with an adolescent and adult formulation combined tetanus, diphtheria, and 5-component acellular pertussis vaccine. Vaccine 25 (2007) 8172-8179.*
Huang et al. Immunogenicity and protective efficacy in rhesus monkeys of a recombinant ORF2 protein from hepatitis E virus genotype 4. Arch Virol. 2009;154(3):481-8. Epub Feb. 25, 2009.*
GenBank: BAG15898.1. capsid protein, partial [Hepatitis E virus]. Dec. 16, 2008.*
Shrivastava et al. Development of candidate combination vaccine for hepatitis E and hepatitis B: a liposome encapsulation approach. Vaccine. Nov. 5, 2009;27(47):6582-8. Epub Sep. 9, 2009.*
GenBank: ACA14202.1. L2 protein [Human papillomavirus type 16]. Feb. 24, 2008.*
Niikura et al. Chimeric Recombinant Hepatitis E Virus-like Particles as an Oral Vaccine Vehicle Presenting Foreign Epitopes. Virology 293, 273-280 (2002).*

* cited by examiner

*Primary Examiner* — Nianxiang Zou
(74) *Attorney, Agent, or Firm* — Seyfarth Shaw LLP

(57) ABSTRACT

Vaccine combinations which comprise at least two or more of the following antigens: DTap-HEV-HepB-HPV suitable for administration in humans. A number of variations in the combination of these antigens have been disclosed that is suitable for concomitant administration. The methods of preparing the vaccine combinations are disclosed. Nucleic acids encoding the antigens, as well as methods for their production and use are provided.

18 Claims, 4 Drawing Sheets
(3 of 4 Drawing Sheet(s) Filed in Color)
Specification includes a Sequence Listing.

VACCINE COMBINATIONS

This application is a national phase application under 35 U.S.C. § 371 of International Application No. PCT/IN2013/000306, filed May 9, 2013, which claims priority to Indian Patent Application No. 486/CHE/2012, filed on May 9, 2012 the disclosures of which are both hereby incorporated by reference

FIELD OF INVENTION

The invention relates to a combination vaccine and uses thereof.

BACKGROUND OF THE INVENTION

The incidence of Human papillomavirus (HPV) infections is high in the developing countries. In India, more than 134,000 new cases and nearly 74,000 deaths due to cervical cancer are reported every year according to the report of the WHO/ICO HPV Information Centre, June 2010.

In India, cervical and breast cancer are most frequent among the cancer cases in women particularly in the age group of 15-44 years. About 7.9% of women in the general population harbor HPV infection and most incidences of invasive cervical cancers are caused by HPV16 and HPV18. Mixed infections with other HPV genotypes are common Candidate vaccines that confer broad protective efficacy against multiple genotypes is the way forward for effective HPV vaccination. The HPV vaccines using the L1 capsid proteins are type specific for HPV16, HPV18, HPV6 and HPV11 and fail to offer complete protection against infection caused by other genotypes such as HPV31, HPV35, HPV52, HPV58 etc. which are also associated with progression of HPV infection to cervical carcinoma. There are no HPV vaccines available commercially as yet, that offers cross protection against infection by multiple HPV genotypes. Two preventive vaccines comprising recombinant HPV L1 virus-like particles (VLPs) have been licensed. They target only two of the approximately 15 known oncogenic HPV types. Nearly 70% of cervical cancer cases are attributed to HPV16 and HPV18, and there is evidence for some degree of cross-protection against the other closely related genotypes of HPV. Other approaches to the development of broadly protective HPV vaccines include multi-valent vaccines using L1 capsid protein of at least nine HPV oncogenic viruses, with no added cost advantage and hence the cost of these vaccines would preclude sustained global delivery particularly in third world countries where the incidence of HPV infection is high. Other approaches have used the HPV L1 antigens in combination with HPV L2 capsid protein which have broadly neutralizing epitopes. However, the L2 capsid protein is by itself poorly immunogenic necessitating alternate strategies of combining the epitopes derived from L2 protein in combination with HPV L1 capsid protein, or in combination with other viral antigens that have the ability to assemble into Virus-Like Particles (VLPs). The rationale for design of such chimeras is for increasing the epitope density of the heterologous peptides on the backbone of the VLPs thereby increasing their immunogenicity. Chimeric constructs of HPV16 L2 epitopes with the HbsAg (Hepatitis B surface antigen) to assemble into virus like particles (VLPs) has been described in PCT/IN2009/000333.

Hepatitis E virus (HEV) is an enterically transmitted virus that is responsible for endemic hepatitis as well as sporadic acute hepatitis. HEV-infected persons exhibit a wide clinical spectrum ranging from asymptomatic infection to fulminant hepatitis. The clinical features of hepatitis E virus with icterus, high fever, hepatomegaly, and pruritus are similar to those of acute viral hepatitis caused by other hepatotropic viruses. The viral infection is commonly diagnosed by laboratory findings of elevated serum bilirubin, increase in liver enzymes and mild increases in alkaline phosphatase activity. The incidence of HEV is high in the developing countries (Emerson and Purcell, 2007; Chandra et al., 2008). HEV is an important aetiological agent for sporadic fulminant hepatic failure (FHF) in developing countries [Nanda et al., 1994]. The HEV infection accounts for more than 50% of acute viral hepatitis cases with a case fatality of 0.2% to 4% in the general population and upto 20% in pregnant women especially during the third trimester of pregnancy (Guu et al., 2009). High mortality, particularly during the third trimester of pregnancy, following fulminant hepatic failure, is characteristic of HEV infection in pregnant women (Khuroo et al., 1981) and may be related to hormonal changes in pregnancy (Lindemann et al., 2010). In studies involving pregnant women, it was shown that HEV accounted for nearly 37% of acute viral hepatitis infection and 81% of cases of fulminant hepatitis (Beniwal et al., 2003). An obstetric complication, such as premature rupture of membranes and intrauterine growth restriction is common during HEV infection is pregnancy [Kumar et al., 2004]. In HEV infection during third trimester of pregnancy, death is usually due to fulminant hepatitis or obstetric complications (Tsega et al., 1993). Vertical transmission of the virus with consequent morbidity and mortality of infants is also common with third trimester hepatitis E infections (Khuroo et al., 1995). The reasons for high mortality in pregnant women have not been understood clearly. HEV infection may also be associated with severe disease in persons with preexisting liver disease [Kumar Acharya et al., 2007]. Chronic infection with HEV is rare, but is more frequent in HIV-infected persons [Dalton et al., 2009]. Hepatitis outbreaks in developing countries have been caused primarily by HEV genotype 1. Epidemic outbreaks in Mexico and Western Africa were caused by genotype 2. Sporadic cases in Asia were caused by genotype 4. So far only genotypes 1 and 2 have occurred in humans, whereas genotypes 3 and 4 have also been isolated in animals. HEV has only one serotype (Mushahwar, 2008) which means that a candidate vaccine of one genotype can cross protect infection caused by other genotypes of the HEV. The use of Hepatitis E virus antigens including the ORF2, either the full length or truncated protein is known in the prior art (Amini-Bavil-Olyaee et al., 2009). The use of HEV viral antigens as vaccine for prophylaxis of HEV infection has been disclosed. A recombinant vaccine of HEV ORF2 that has been produced in *E. coli* has also been found to be safe for administration in humans (Zhu et al., 2010). A combination of the Hepatitis E and HPV vaccines for comprehensive healthcare of women is not disclosed in the prior art. Hence it was required to be demonstrate experimentally the feasibility of developing a combination vaccine where there is no antigenic interference when the hepatitis virus and HPV antigens are administered concomitantly either as an admixture that is mixed extemporaneously or as a chimeric antigen that carries both the vaccine epitopes in a single polypeptide expressed as a virus like particle (VLP). The development and use of such combinations is not known in the prior art.

The common problem that is encountered in the development of chimeric vaccines with the other viral antigens is the limitation of the scaffold antigen to accommodate heterologous protein sequences without affecting the native structural conformation that is required for immunogenicity of both the vaccines, especially if it were to be assembled as a virus like particle. Apart from the scaffold antigen, the sequence and the structural conformation of the heterologous protein for preparing the chimeric antigen is important. Also critically important is the location on the scaffold antigen where the heterologous sequence is to be added. Hence these factors cannot be pre-determined until the chimeric constructs are made and tested. To put it simply, what works for a pair of antigens would not be identical to another pair of antigens and hence this information cannot be extrapolated from the prior art describing similar design of chimeric antigens. The full length ORF2 protein of Hepatitis E consists of 660 amino acids. The neutralizing epitopes of the virus are not present largely at the N-terminus and C-terminus of the protein. Large amino acid deletions at the N- and the C-terminus do not diminish the ability of the protein to assemble into VLPs. Rational design of HPV-HEV chimeras involve the insertion of the heterologous HPV L2 broadly neutralizing epitopes in any region of the HEV ORF2 protein that does not affect the native structure of the protein and without compromising the immunogenicity of both the viral antigens. The insertion of the HPV L2 epitopes of desired sequences into any region of the HEV ORF2 protein that does not diminish the ability of the HEV antigen to assemble into VLPs, and at the same time display the heterologous HPV L2 epitopes on the surface of the chimeric VLP would be an ideal choice for vaccines against both HPV and HEV. A combination of HEV antigens with HEV-HPVL2 chimeric antigen and/or with the HPV16 and HPV18 L1 capsid antigens as an admixture of the two antigens is also a very effective vaccine combination. Addition of HbsAg or chimeric HbsAg-HPVL2 whose method of production is described in PCT/IN2009/000333 to the HEV and/or HEV-L2 antigens is also not known in the prior art. ORF3 of HEV which is also an immunogenic structural protein is a good vaccine candidate that can be included as an antigen in such a vaccine combination. The addition of Tdap or DTap (diphtheria toxoid, tetanus toxoid and acellular pertussis antigens) or DTwP, wherein the acellular pertussis antigens are replaced by whole cell pertussis antigens to the aforementioned vaccine antigens is also novel and is not described in the prior art. The discovery and development of such vaccine combination is also very significant for the reasons mentioned below.

The mortality rate due to neonatal tetanus is high globally and especially so in the developing countries. It is easily preventable as antibodies against tetanus toxin are actively transported by the placenta from the immunized mother to her fetus. This provides passive protection against tetanus during the neonatal period and for a few months following birth. The mortality rate due to neonatal tetanus can be reduced with immunization of pregnant women or in women of childbearing age. It has been demonstrated that the use of two or more doses of tetanus toxoid during pregnancy could prevent neonatal tetanus (Schofield et al., 1961) Tetanus toxoid vaccination of pregnant women has been included in the WHO's Expanded Program on Immunization. Similarly, vaccination with Tdap (tetanus toxoid, reduced diphtheria toxoid, and acellular pertussis) vaccines is also recommended for pregnant women. It is recommended that one dose of Tdap be administered during the third trimester or late in the second trimester (after 20 weeks gestation). If not administered during pregnancy, Tdap should be administered immediately postpartum. When Tdap is administered during pregnancy, at time of delivery the mother will be protected, making her less likely to transmit pertussis to her infant, and transplacental maternal antibodies will likely protect the infant against pertussis in early life. The preferred schedule in pregnant women is two doses of Td separated by 4 weeks, and a dose of Tdap 6 months after the second dose (post-partum). It is recommended that adolescents and/or women of active child bearing age should receive a dose of Tdap preferably before pregnancy. Whole cell pertussis vaccine can also be administered in lieu of acellular pertussis vaccine. Hence Tdap and/or tetanus toxoid vaccines are a good option to be included in the combination vaccine for women along with HPV and HEV antigens.

Such a combination vaccine for Hepatitis E with tetanus toxoid or with Tdap with and without HPV antigens is novel and is not commercially available or it is disclosed in any prior art. In the current invention, methods are disclosed on the development of a combination vaccine of HEV and HPV. The rationale for combining the aforementioned antigens either in a single formulation as an admixture, or administered concomitantly is to improve the overall health outcome in women, as cervical cancer ranks high as the most frequent cause of cancer among women in India, and also for the fact that hepatitis E infection causes high mortality in pregnant women particularly in the third trimester of pregnancy. The HPV-HEV vaccine combination can be expected to decrease the mortality and morbidity due to HPV and HEV infections and to improve the overall health in this segment of the population and as recommended, vaccination with Tdap to pregnant women reduces infant mortality due to tetanus and pertussis. Such combination vaccines are not only useful to provide protection against multiple pathogens, but are very desirable as they reduce the number of immunizations required. Combination vaccines also help to lower the manufacturing and distribution cost, making the vaccines cost-effective and affordable. Affordability of vaccines increases acceptance and coverage rates. The use of suitable adjuvants in the vaccine formulations also reduces the amount of antigen required and helps in the manufacture of low-cost vaccines thus conferring a distinct economic advantage. No antigenic interference has been observed with the co-administration of all the aforementioned antigens and hence combination of different antigens can be made. For the production of recombinant antigens, *Pichia pastoris* as recombinant expression host is advantageous at industrial scale as it is cost effective for large scale manufacture compared to other eukaryotic expression systems. Recombinant proteins derived from *Pichia pastoris* have been successfully commercialized and have been found safe for human use. Use of this expression system for the manufacture of both the HPV and HEV antigens is therefore safe and highly cost-effective for production of vaccines for HPV and HEV.

OBJECT OF THE INVENTION

Primary object of the invention is to provide vaccine combinations for prophylaxis and treatment of viral and bacterial infections.

Another object of the invention is to provide a combined vaccine for HPV, HEV and Hepatitis B infections.

Another object of the invention is to provide a combination vaccine of HPV-HEV-Hepatitis B antigens additionally comprising tetanus toxoid and/or the trivalent tetanus toxoid and/or reduced diphtheria toxoid and/or pertussis vaccines.

Another object of the invention is to provide sequences of the recombinant antigens of and HEV and the chimeric HPV-HEV antigens.

Another object of the invention is to provide the methods of development of such combination vaccines.

A further object of the invention is to provide a method of testing such combination vaccines in mammals.

Another object of the invention is to provide adjuvanted vaccine compositions of the aforementioned antigens.

A further object of the invention is to provide the HPV and HEV antibodies for diagnosis of the HPV and HEV viral infections.

SUMMARY OF THE INVENTION

Accordingly, there are provided vaccine combinations of DTap-HEV-HepB-HPV antigens in a number of variations in the combinations of these antigens with tetanus toxoid and/or the trivalent tetanus toxoid and/or reduced diphtheria toxoid and/or pertussis antigens.

The invention provides vaccine composition of a combination of antigens of human papillomavirus (HPV) and hepatitis E (HEV) for the prophylaxis, treatment and diagnosis of HPV and Hepatitis E virus infections in mammals, particularly humans. Further, the combination of hepatitis B antigen, tetanus toxoid and/or Tdap (tetanus toxoid, reduced diphtheria toxoid, and acellular pertussis) vaccine to the aforementioned vaccine combination is also within the scope of the invention.

Adjuvanted vaccine compositions of the aforementioned virus antigens offer high protective efficacy. Such combination vaccine may be supplied in one container in a single combined formulation suitable for injection, or in different such containers (vials). Such vaccine compositions are administered by mixing the required amount of antigens extemporaneously in a single container before administering to a host as an injection. The combination of the aforementioned vaccines with other viral and bacterial antigens is also within the scope of the invention.

In one embodiment, the invention provides combination vaccine of purified HPV16 and HPV18 L1 antigens with purified HEV ORF2 antigen.

In another embodiment, the invention provides combination of HPV16, HPV18 L1 proteins and HPV16L2-HbsAg chimeric antigen in combination with HEV antigen.

In another embodiment, the invention provides chimeric HEV-HPVL2, and HPV16 and HPV18 L1 antigens which are useful for the prophylaxis of both the viral infections.

In an exemplary embodiment, vaccine composition of the invention comprises: a diphtheria toxoid, 'D'; a tetanus toxoid, 'T'; pertussis antigens; recombinant hepatitis B virus surface antigen, HBsAg; recombinant human papillomavirus L1 antigens of HPV16 and HPV18; recombinant hepatitis E (HEV) ORF2 antigen; recombinant HPV L2 epitope in chimeric fusion with HBsAg or Hepatitis E (HEV) protein. No antigenic interference is observed with the combination of aforementioned antigens.

The vaccines of the invention can be prepared extemporaneously at the time of use by mixing together two components: (a) a first component comprising HEV, HPV and chimeric HEV or HBsAg antigens; and (b) a second component comprising Tdap.

The two components are filled separately and thus in general, the invention provides a kit comprising: (a) a first component comprising HEV, HPV and chimeric HEV or HBsAg antigens; and (b) a second component comprising Tdap.

Alternatively Tdap can be formulated in aluminum hydroxide and used as a single component vaccine.

If packaged separately, the mixing step will typically take place at the time of use. Thus the invention provides a process for preparing a vaccine composition of the invention, comprising the steps of (a) providing a first component comprising HEV, HPV and chimeric HEV or HBsAg antigens and (b) providing a second component comprising Tdap antigens (c) mixing the first and second components to give the vaccine.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
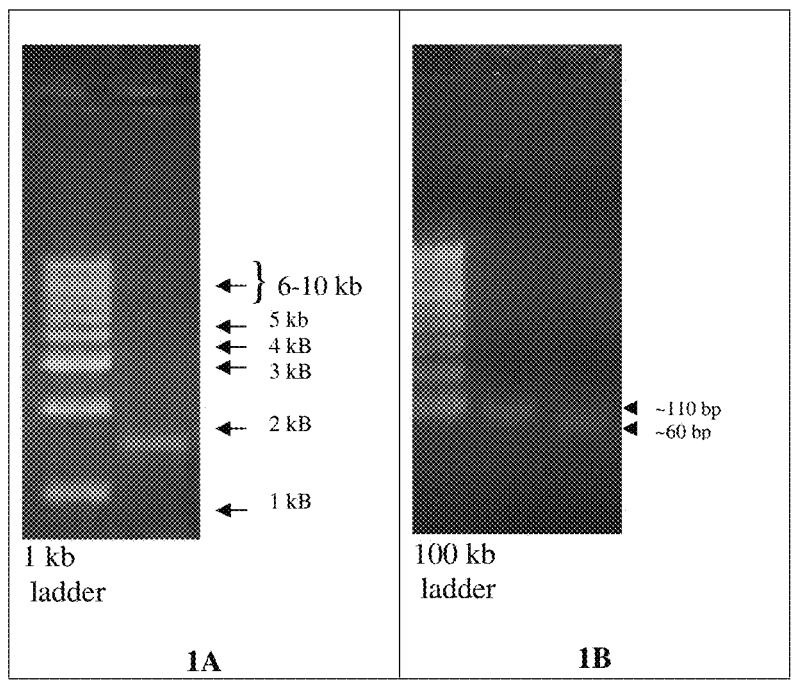
FIG. 1: PCR amplification of (1A) approximately ~1.494 Kb of HEV ORF2 gene (1B) ~110 bp (that includes the gene sequence, restriction enzyme sequence and the 5' overhang) corresponding to the amino acid SATQLYKTCKQAGTCP-PDIIPKVEG of HPV16 L2 and ~60 bp (that includes the gene sequence, restriction sequence and the 5' overhang) corresponding to the amino acid sequence LVEETSFIDA-GAP of the HPV L2 epitopes by PCR using gene specific primers described in Example 1. The size of the amplified gene fragment is shown against the 1 Kb ladder fore HEV ORF2 and against 100 bp ladder for HPVL2 fragment.

Detailed embodiments of the present invention are disclosed herein below. However, it is to be understood that the disclosed embodiments are merely exemplary of the invention, which can be embodied in various forms. The scope of the invention is not limited to the disclosed embodiments and terms and phrases used herein are not intended to be limiting but rather to provide an understandable description of the invention. The invention is defined by claims appended hereto.

The invention relates to vaccine composition that includes a combination of antigens of human papillomavirus (HPV) and hepatitis E virus (HEV) for the prophylaxis and diagnosis of HPV and Hepatitis E virus infections in mammals, particularly humans. Addition of Hepatitis B antigen to the above combination is included in the scope of the invention. Furthermore, the combination of tetanus toxoid and/or Tdap (tetanus toxoid, reduced diphtheria toxoid, and acellular pertussis) vaccine to the aforementioned vaccine combination is also within the scope of the invention. Such vaccine compositions are administered by mixing the antigens extemporaneously in a single container before administering to a host as an injection, or can be concomitantly administered in humans in two or more separate formulations that can be injected parenterally at different sites for eliciting immune response. A combination vaccine of the aforementioned antigens is supplied in a single container such as a vaccine vial or in a pre-filled syringe ready for injection. The combination of the aforementioned vaccines with other viral and bacterial antigens is also within the scope of the invention.

The invention also provides a process for preparing a combination vaccine that comprises (i) a hepatitis E (HEV) virus like particle, (ii) a chimeric protein of hepatitis B virus surface antigen HbsAg with HPV L2 protein ('HbsAg-HPVL2'), and/or chimeric HEV-HPV L2 chimeric protein (iii) HPV16 L1 and HPV18 L1 antigens (iv) tetanus toxoid ('T'), (iii) acellular pertussis antigens ('aP'), (vi) diphtheria toxoid ('D') and the process includes the steps of (a) combining the HEV component to the chimeric HEV-HPVL2 component to get a bivalent component (b) combining the HEV antigen to the chimeric HbsAg-HPVL2 to get a bivalent component (a) combining the HEV component to HPV16 L1 and HPV18 L1 components to get a trivalent HEV-HPV16L1-HPV18L1 component (a) combining a trivalent HEV-HPV16L1-HPV18L1 component with a monovalent chimeric HEV-L2 component, to get a tetravalent HEV-HPV16L1-HPV18L1-HEV-L2 component; (b) combining a trivalent HEV-HPV16L1-HPV18L1 component with chimeric HbsAg-HPVL2 to get a tetravalent HEV-HPV16L1-HPV18L1-HbsAg-L2 component and (c) mixing the D-T-aP-component with either of the bivalent/trivalent/tetravalent components for a combination vaccine/or concomitantly administering the D-T-aP vaccine along with the viral vaccines parenterally to a mammalian host.

The HPV capsid antigens of the combination vaccine are highly immunogenic when expressed as recombinant proteins in a eukaryotic expression system and are purified therefrom. The HPV antigens are derived from the major capsid protein L1 that is expressed as virus like particles (VLPs). HPV antigens include two or more antigens selected from a list of 'oncogenic' HPV types including HPV16, HPV18, HPV31, HPV33, HPV35, HPV39, HPV45, HPV51, HPV52, HPV56, HPV58, HPV59, HPV68 etc and could include the HPV L2 capsid protein from any of the above mentioned HPV types Chimeric protein of HPV L2 capsid and HbsAg is a good vaccine candidate for use in combination vaccine with HEV and other HPV antigens. Additions of heterologous viral and bacterial epitopes that are fused to the aforementioned vaccine antigens also augment the immunogenicity of the HPV vaccine.

The hepatitis E vaccine antigens are those encompassing the full length or the truncated sequence of Open Reading Frame 2 (ORF2) of protein which is a structural protein of the Hepatitis E virus. Truncations of the HEV full length ORF2 protein were made to result in better expression with increased stability and without compromising the immunogenicity of the candidate antigen to assemble into VLPs. Truncated sequences of the HEV ORF2 such as 112-608 amino acid region and alternatively 368-606 amino acids were so designed to accommodate heterologous viral sequences without compromising the structural conformity required for eliciting strong immune response. From the full length sequences of HEV ORF2 protein such as in SEQ ID NO.1 and the full length protein of HPV16 L2 such as in SEQ ID NO. 2, different truncated gene fragments that encompass the major neutralizing epitopes of both the antigens were generated by PCR and several chimeric constructs were made by ligating the fragments together. The HEV gene sequences can be derived from any HEV genotype such as genotypes 1-4. The different sequences of the chimeric antigens are within the scope of the invention. Such constructs code for the chimeric proteins of different molecular sizes. No antigenic interference was observed with the combination of aforementioned antigens. It was found that the vaccines of the invention can be prepared extemporaneously at the time of use by mixing together two components: (a) a first component comprising HEV, HPV and chimeric HEV or HBsAg antigens; and (b) a second component comprising Tdap. The two components are filled separately, and thus in general the invention provides a kit comprising: (a) a first component comprising HEV, HPV and chimeric HEV or HBsAg antigens; and (b) a second component comprising Tdap. Alternatively Tdap can be formulated in aluminum hydroxide and used as a single component vaccine along with the viral antigens. If packaged separately, the mixing step will typically take place at the time of use. Thus the invention provides a process for preparing a vaccine composition of the invention, comprising the steps of (a) providing a first component comprising HEV, HPV and chimeric HEV or HBsAg antigens and (b) providing a second component comprising Tdap antigens (c) mixing the first and second components to give the vaccine.

With the aforementioned combination vaccine it was possible, to obtain antibody titers against HPV and HEV virus approaching or equivalent to, or in excess of 100% of the titer obtained when the antigen is administered in isolation to animals. The combination vaccine elicited robust antibody levels against both HPV and HEV virus infections and no antigenic interference was observed. All the methods described in the invention are applicable to any genotype or genotypic variants/serotypes/strains of HPV and Hepatitis E virus. Within the scope of the invention are the compositions and methods of preparing and using the HPV and HEV antigens of defined sequence expressed as recombinant proteins or recombinant virus like particles in any prokaryotic or eukaryotic expression system. The gene sequences are the native viral sequences or synthetic genes that are codon optimized for expression in the host cells. The eukaryotic expression system of choice includes mammalian cells; baculovirus mediated expression in insect cells, and yeast cells of any species, most preferably *Pichia pastoris* or *Saccharomyces cerevisiae*. *Pichia pastoris* was found to express the aforementioned antigens to a high level. Optimization of the sequence for eukaryotic expression includes the presence of Kozak's consensus sequence such as (gcc) gccRccATGG at the 5' end of the gene, where the ATG is the initiation codon, or the use of yeast consensus sequence (5'-[A/T]TTTAT[A/G]TTT[A/T]-3'). For expression in *Pichia pastoris*, the synthetic gene sequences were codon optimized to further increase the expression levels. The aforementioned proteins were expressed either as intracellular protein and purified therefrom. Alternatively they can be expressed as secretary proteins and purified. Any suitable expression vector is selected from the list that includes but is not limited to pPIC3.5, pPIC3.5K, pA018, pPIC9, pPIC9K, PHIL D2 etc. for expression in yeast cells. Any plasmid vector suitable for expression in *Saccharomyces cerevisiae* or any other species of yeast are used. The yeast cells include the following but are not limited to *Pichia pastoris, Saccharomyces* spp, *Hanensula polymorpha, Schizosaccharomyces* spp, *kluveromyces* spp. Either of the *Pichia pastoris* strains such as GS115, KM71 and protease deficient strains such as SMD1168 or SMD1163 is used for recombinant expression. The aforementioned genes are cloned either in single copy or in more than one copy. The antibodies against the HPV and HEV virus antigens are used for developing methods for estimation of antigen content by ELISA and also for use as a reference standard while estimating vaccine antibody titer. They find application in diagnosis also.

Purification of the virus was achieved by physical or chemical means and preferably by a combination of both. Physical methods utilize the physical properties of the virus like particles such as density, size, mass, sedimentation coefficient etc. and include any of the following techniques but are not limited to: ultracentrifugation, density gradient centrifugation, ultrafiltration etc. Purification through chemical means employs methods such as adsorption/desorption through chemical or physiochemical reactions such as ion exchange chromatography, affinity chromatography, hydrophobic interaction chromatography, gel filtration chromatography, hydroxyapatite matrix, salting with inorganic salts one such example being ammonium sulphate, and by the use of proprietary Himax technology, organic salts, organic solvents, aluminum phosphate, aluminum hydroxide and organic compounds such as polyethylene glycol. Purification of the recombinant antigens of the virus was achieved by either one or a combination of two or more of the above mentioned methods.

The antigenic compositions of the above mentioned HPV-HEV vaccine and HPV-HEV and tetanus toxoid and Tdap vaccines were formulated in pharmaceutically acceptable carrier that is suitable for immunization in human. Furthermore, for adjuvanted vaccine formulations, suitable adjuvants were selected from the following list, which includes but is not limited to: aluminum hydroxide, aluminum phosphate; calcium phosphate; inulin of any polymorphic form, preferably gamma inulin; adjuvants containing inulin in combination with other organic and inorganic compounds such as aluminum hydroxide, aluminum phosphate, aluminum sulphate phosphate and calcium phosphate; liposomes, chitosan and complex carbohydrates such as dextran, dextrins, starch, mannans and glucomannans, galactomannans, beta-glucans, heparin, cellulose, pectins and pectinates, lectins and any other carbohydrates either synthetic or derived from any source, any biodegradable and biocompatible polymers, such as poly lactide and poly(lactide co-glycolides; PLG) or PLGA; any emulsions including but not limited to oil in water emulsions, other squalene based adjuvants, oil in water emulsion containing cholecalciferol, cholecalciferol by itself as an adjuvant, any water in oil emulsion; liposomes prepared with cholecalciferol as one of the ingredients along with other lipid soluble compounds; liposomes of other compositions; RIBI adjuvant systems, saponins including but not limited to QS-21, QuilA, tomatine, ISCOMs, ISCOMATRIX etc, lipopeptides, glycopeptides, lipopolysaccharides, muramyl dipeptides and any peptide based adjuvants, oligonucleotides, any TLR ligands as adjuvants, any cytokine, vitamins and non-toxic bacterial toxins etc. In addition to the above, any other organic and inorganic substances that have good immunopotentiating activity can be used as adjuvants either singly or in combinations to enhance the immunogenicity of the HPV-HEV combination vaccines. The vaccine combinations with alum elicited strong immunological response when administered parenterally, in animals. The methods and vaccine compositions containing vaccine adjuvants are within the scope of the invention.

For potency testing of the vaccine, the vaccine formulations were tested in mice and guinea pigs. The resultant serum was assayed in vitro by estimation of antibody titer by ELISA. Toxin neutralization test was used for evaluation of potency of tetanus toxoid and diphtheria toxoid by procedures well described in literature. Seroconversion was observed in the animals immunized with the vaccine formulations described in the present invention. No antigenic interference either due to combination of different antigens or by adjuvant was observed. The buffer used in the formulations is phosphate buffer Phosphate-citrate buffer or any other pharmaceutically acceptable buffer of appropriate pH can be used. 2-phenoxyethanol was used vaccine preservative; thiomerosol or any other vaccine preservative can be used. Alternatively the vaccine combination can be formulated without any vaccine preservative. The vaccines optionally contain stabilizer(s) etc. The excipients were selected from a list that includes but is not limited to non-reducing sugars, sugar alcohols such sorbitol and mannitol, glycerol, amino acids, human serum albumin, and a choice of adjuvant from the aforementioned list of adjuvants. A stable formulation of the immunogen either in a liquid or in a lyophilized form and after reconstitution in a pharmaceutically acceptable buffer or water is suitable for administration parenterally in human host. More specifically, for antigens of the present invention, a diagnostic assay with high sensitivity and specificity for detecting infection are provided. The methods in the scope of the invention are applicable to any genotype/genotypic variants/serotype/strain of HPV and hepatitis E viruses.

EXAMPLES

The invention is further described in following examples.

Example-1: Cloning and Recombinant Expression of Hepatitis E (HEV) Viral and Chimeric HEV-HPVL2 Antigens A synthetic gene of the Hepatitis E ORF2 gene of amino acid sequence of SEQ ID NO.1 was amplified by PCR with 5'primer and 3' primer containing EcoR1 and Not1 restriction sites respectively to obtain a ~1494 bp PCR fragment of SEQ ID NO.3 that encodes the protein of SEQ ID NO. 4. (see FIG. 1). The primers used for PCR amplification of the HEV gene are 5'-CATTTGAATTCACCATGGCCGTTG-CACCTGCTCATGATAC-3' and 5'-TATCGCGGCCGCT-CATTAAGCCAATGCAGAATGAGGAGC-3'.

The conditions for PCR amplification were denaturation at 94° C. for 45 seconds, annealing at 60° C. for 40 seconds and extension at 72° C. for 2.5 minutes for 30 cycles followed by final extension at 72° C. for 10 minutes. The reaction mix consisted of 1× Taq DNA polymerase buffer, 0.25 mM dNTPS, 20 picomoles of each primer and 1 U of Taq DNA polymerase (Genei) and 1 U of Pfu DNA polymerase (New England Biolabs). The PCR fragment was digested with EcoR1 and Not1, gel purified and used for ligation to EcoR1 and Not1 digested yeast vector pPIC3.5K (Invitrogen, Carlsbad, USA). The 1494 bp PCR fragment was used for the chimeric fusion with gene sequence for HPV16 L2 epitopes consisting of 14-37 amino acids of the sequence SATQLYKTCKQAGTCPPDIIPKVEG and/or 108-120 amino acids of the sequence LVEETSFIDAGAP of the HPV16 L2 protein of SEQ ID NO 2 Chimeric fusion of the gene sequence for HPV16 L2 epitope 14-37 amino acids generated SEQ ID NO. 5 encoding SEQ ID NO.6 when ligated to the 5'end of HEV gene, and SEQ ID NO.7 encoding SEQ ID NO.8 when it was ligated to the 3' end of the of the HEV ORF2 PCR fragment. The ligation was achieved with a BamH1 site located at either end of the primers for HEV or HPV L2 sequence. The following primers were used for amplification of 14-37 amino acids of the HPV16 L2 sequence for fusion at the N-terminus of the HEV ORF2 fragment: 5'-ATGTCGAATTCACCATGGCT-GCAACTCAGTTGTATAAAAC-3' and 5'-ATCGAG-GATCCTTGAACCTTTGGGATAATGTC-3'. For amplification and fusion at the C-terminus of the HEV ORF2 fragment, the following primers were used for HPV16 L2 PCR of the above region: 5'-ATGTCGGATCCTCTG-CAACTCAGTTGTATAAAAC-3' and 5'-ATCGAGCGGC-CGCTCATTAACCTTCAACCTTTGGGATAATGTC-3'. PCR primers that were designed to amplify the 5' TTGGT-TGAAGAAACCTCCTTTATTGACGCTGGTGCTCCA-3' region of HPV16 L2 gene corresponding to the protein sequence LVEETSFIDAGAP also contained a BamH1 site for ligation of the two gene fragments. Chimeric fusion of the gene fragment encoding LVEETSFIDAGAP to the C-terminus of HEV ORF2 resulted in SEQ ID NO. 9 encoding SEQ ID NO.10. The SEQ ID NO.11 is nucleotide sequence of HEV ORF2 with HPV L2 14-37 amino acid region at the N-terminus and HPV16 L2 108-120 amino acids at the C-terminus. The corresponding protein sequence is SEQ ID NO.12. Similarly, for generating chimeric constructs of HEV ORF2 with the aforementioned HPV L2 sequences, PCR primers for amplification of the 1494 bp fragment also included a BamH1 site either at the end of the 5' region or at the 3'end of the gene fragment to facilitate ligation to the HPV L2 epitopes. Alternatively construction of chimeric constructs of Hepatitis E with HPV L2 protein, a 714 bp fragment (from 368-606 amino acids) of ORF2 was amplified by PCR and ligated to HPV16 L2 epitopes (region 14-37 amino acids and/or 108-120 amino acids) either at the N-terminus or at the C-terminus of the HEV PCR fragment. For ligation at the N-terminal end, the HEV fragment was amplified with the primer 5'-ACGTCGGATCCATCGC-CCTTACATTGTTTAATTTG-3' and 5'-TATCGCGGC-CGCTCATTAAGCCAATGCAGAATGAGGAGC-3' and for ligation at the C-terminal end of the HEV fragment, the HEV gene was amplified with 5'-AGCTCGAATTCAC-CATGGCCCTTACATTGTTTAATTTG-3' and 5'-ACTCA-GGATCCTTATCAAGCCAATGCAGAATGAGGAGC-3'. The conditions for PCR amplification were denaturation at 94° C. for 45 seconds, annealing at 56° C.-62° C. for 40 seconds for various primer combinations and extension at 72° C. for 2 minutes for 30 cycles followed by final extension at 72° C. for 10 minutes with reagents of the same concentration as mentioned above for 1494 bp HEV ORF2 amplification. For the generation of the chimeric genes of HPV L2 and HEV, the PCR amplified genes were ligated after BamH1 digestion, further digested with EcoR1 and Not1 and ligated into the EcoR1 and Not1 digested pPIC3.5K yeast vector and transformed in E. coli DH5α. The recombinant plasmid DNA was isolated from transformed E. coli selected on 50 µg/ml ampicillin. The recombinant plasmid containing the HEV-HPVL2 chimeric gene was linearized with BglII and transformed in Pichia pastoris GS115 cells as per the standard yeast transformation protocols (Invitrogen, Carlsbad, USA).

Example-2: Purification of the HEV and HEV-HPV L2 Chimeric Proteins

Figure 2:
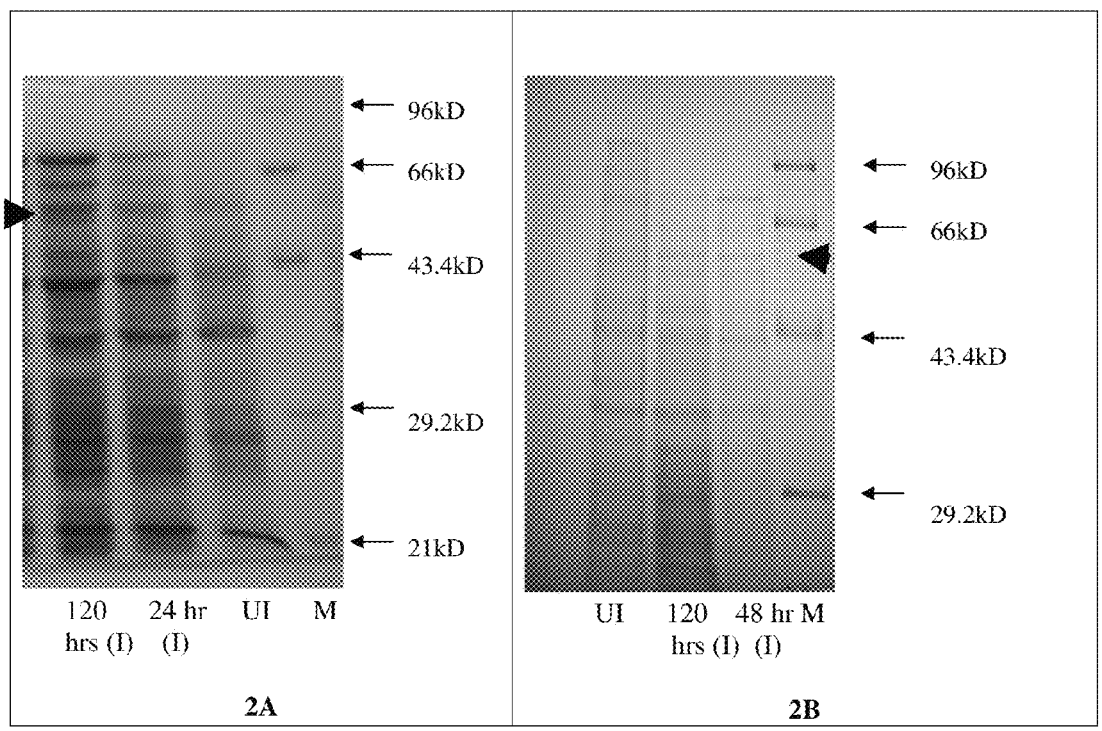
FIG. 2: 2A represents Expression of HEV ORF2 of SEQ ID NO. 4 in *Pichia pastoris* at 24 hrs and 120 hrs after induction (I) with methanol showing the expression of 54 kDa protein; UI—uninduced cells; 2B represents Expression of HEV-HPVL2 of SEQ ID NO. 6 in *Pichia pastoris* at 48 hrs and 120 hrs after induction (I) with methanol showing the expression of the 56 kD protein; UI—uninduced cells; M—is the medium range molecular size marker (Genei, Bangalore).
Figure 3:
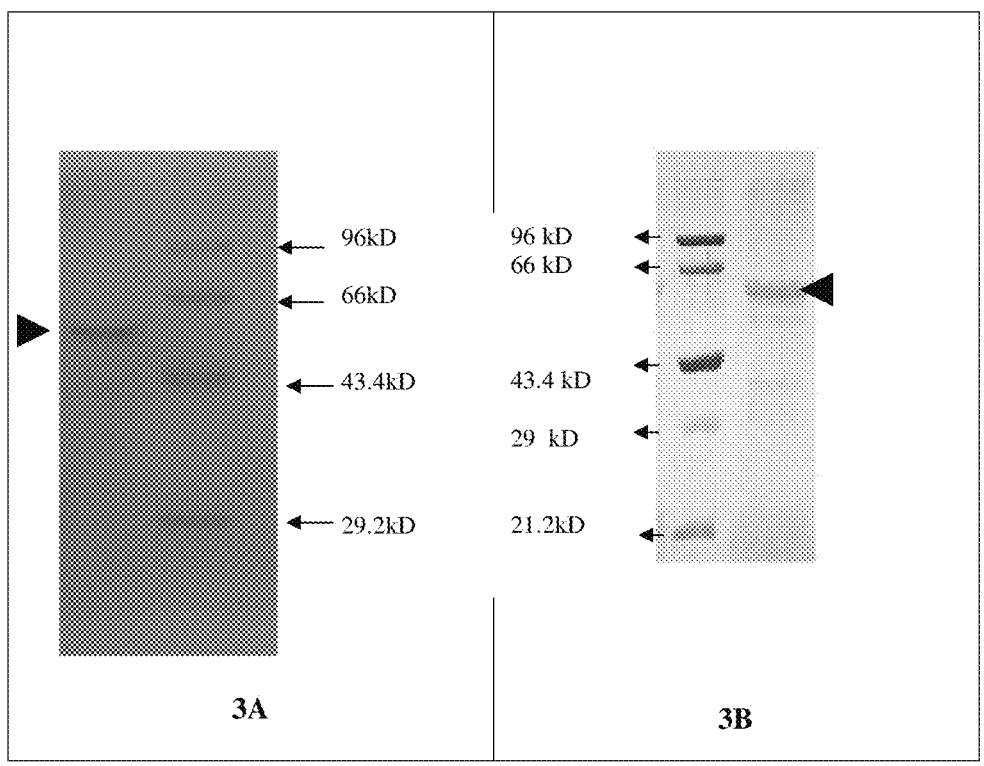
FIG. 3: 3A represents Purified recombinant 54 kD HEV ORF2 protein of SEQ ID NO.4 indicated by thick arrow; and 3B represents the purified recombinant chimeric 56 kD HEV-HPV16 L2 protein is indicated by thick arrow. The size of the molecular size markers is shown.

The Pichia pastoris GS115 clones expressing the recombinant proteins of HEV and the HEV-L2 chimeric proteins were grown for 96 hours at 280 C and induced with 1% methanol every 24 hours and harvested at the end of 120 hours (FIG. 2). The cells were washed once with 50 mM Tris-HCl buffer pH 8.0 containing 2 mM EDTA, 10 mM NaCl, and lysed in the same buffer containing 0.05% Triton X-100. The cell lysate was centrifuged at 4000 rpm for 20 minutes and the cell supernatant containing the proteins were purified on a Q-sepharose column equilibrated with the same buffer. The proteins were eluted with a salt gradient containing 50 mM to 750 mM NaCl in the same buffer and the fractions containing the protein were pooled and checked on SDS-PAGE gel for the presence of 54 kDa band for the HEV protein and 56 kDa band for the chimeric HEV-HPV16 L2 protein. The fractions containing HEV proteins were concentrated using TFF system and the concentrate was loaded on Captocore700 gel filtration column equilibrated with 50 mM phosphate buffer, pH 7.2 containing 154 mM NaCl. The viruses like particles were collected in the flow through. The purity of the protein was checked on SDS-PAGE gel and found to be more than 95% pure (FIG. 3). The purified proteins were further characterized.

Example-3: Transmission Electron Microscopy

Figure 4:
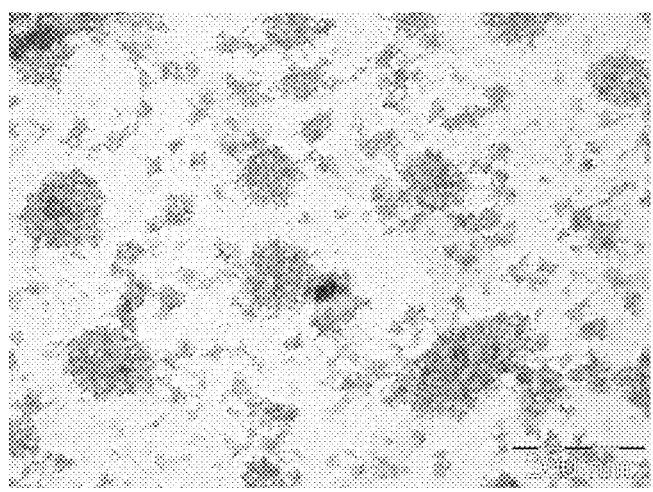
FIG. 4: Represents Transmission electron microscopy (TEM) of the chimeric HEV-HPV16L2 protein stained with uranyl acetate shows the assembly of the protein spontaneously into virus like particles. The size of the bar is 200 nm as shown in the bottom of the picture.

The purified viruses like particles (VLPs) were visualized by Transmission Electron microscopy (TEM) after negative staining with 2% uranyl acetate and is depicted in FIG. 4.

Example-4: Vaccine Formulations for Potency Testing

For potency testing, the following vaccine combinations each consisting of the purified vaccine antigen of the below mentioned concentrations and adjuvant(s) were prepared for immunization in mice: a) 30 µg of HEV ORF2 54 kDa protein, 40 µg HPV16 L1 protein, 20 µg HPV18 L1 protein, and 30 µg HbsAg-HPV L2/HEV-HPV L2 chimeric antigen all adsorbed on 1.5 mg of aluminum hydroxide and Tdap (tetanus toxoid, reduced diphtheria toxin and acellular pertussis) comprising formaldehyde detoxified 2.5 Lf units of diphtheria toxin (DT), 5 Lf units of tetanus toxoid (TT) and 8 µg of detoxified Pertussis toxin (PT), 8 µg filamentous hemagglutinin (FHA) and 2.5 µg of pertactin (PRN) all adsorbed individually on aluminum hydroxide. Alternatively aluminum phosphate at 1.5 mg can be used for the adsorption of all the above antigens except tetanus toxoid that is adsorbed in aluminum hydroxide. The tetanus toxoid (TT) and detoxified Pertussis toxin (PT) are GMP products obtained from the production facility of Bharat Biotech Intl Ltd. The acellular pertussis antigens were purified from the culture supernatant of Bordetella pertussis though steps involving concentration of the culture supernatant, salt fractionation, diafiltration, column chromatography and buffer exchanged into 1×PBS, pH 7.2. The HPV16 and HPV18 L1 antigens are recombinant proteins expressed and purified from Pichia pastoris cells. The method of production of recombinant HPV proteins and HbsAg-HPV16 L2 is previously described in WO2010/001409. Addition of other adjuvants further enhanced the potency of the vaccine preparation. Addition of polymorphic forms of inulin, particularly the gamma inulin enhanced the potency of the vaccines. Gamma inulin comprises particles with a molecular weight of above 8000 daltons and is virtually insoluble in water at 37° C. The high molecular weight inulin Orafti®HPX was obtained from Beneo Orafti, Belgium. Gamma inulin fractions were prepared by the methods outlined in the prior art (U.S. Pat. No. 4,954,622; PCT/AU86/00311) and the preparation of algammulin was as per the methods described by Cooper and Steele, 1991. The gamma inulin and algammulin preparations at a concentration of 2 mg/ml were used in the vaccine formulations. The vaccine antigens were mixed with adjuvants for two hours at ambient temperature and used immediately for injections. Similar formulation was also tested with phosphate-citrate buffer of pH 6.8-7.2 with adverse no effect on stability. Adsorption of the vaccine antigens to alum was tested by centrifuging the formulation and supernatant was checked by SDS-PAGE for protein bands of expected size for different antigens. All the aforementioned antigens adsorbed efficiently to alum. The vaccine formulations were tested in mice for potency.

Example-5: Potency Testing of the Vaccine Formulations

Six Balb/c mice were used per group for testing different viral antigen combinations described in Example 4. The highest vaccine antigen concentration is described in Example 4. Four two-fold dilutions of the vaccine formulations were injected intramuscularly in 6-8 week old mice of 18-20 g body weight. The dilutions were made in 1×PBS (50 mM phosphate buffer, pH 7.2 containing 150 mM NaCl) and containing the appropriate amount of adjuvant in order to maintain a constant adjuvant concentration. 2-phenoxyethanol was used as a vaccine preservative. For control animals, equal volume of buffer containing the same quantity of adjuvant was injected without the viral antigens. A booster injection was given on day 14 after the administration of the first vaccine dose. Blood was collected from retro-orbital sinus 7 days after administration of the booster dose, serum separated, heat inactivated at 560 C for 30 minutes and stored frozen at −800 C until used for serological assays. For testing the potency of diphtheria toxin, guinea pigs were used as described below in Example 6.

Example-6: Determination of Antibody Titer by ELISA and by Toxin Neutralization Assay For estimation of the antibody titer to HEV, and the HEV chimeric antigen with HPV16 L2, the HEV antibodies were estimated by indirect ELISA. About 1 µg of the 54 kD vaccine antigen was coated on 96-well plate in carbonate buffer, pH 9.6 and incubated overnight at 2-8° C. Similarly for estimation of antibody titer to HPV16 and HPV18 L1 antigens and the HPV16 L2 epitopes, 1 µg of the purified HPV16 L1 and HPV18 L1 and HPV16 L2 antigens respectively were coated in 96-well plates in carbonate buffer, pH 9.6 incubated overnight at 2-8° C. The rest of the procedure for the above HEV and HPV antigens are same as described below. After discarding the plate contents, the wells were blocked with 3% skimmed milk powder in phosphate buffered saline, pH 7.4. The plates were incubated at 37° C. for one hour and were washed with the washing buffer containing 0.05% Tween-20 in PBS (PBST) five times. Serial two fold dilutions of the test sera were added and the plates were incubated at 37° C. for one and half hours. The plates were washed eight times with the wash buffer. The mouse anti-IgG HRPO conjugate was added at 1:2500 dilution and incubated at 37° C. for one hour. The wells were washed five times with wash buffer and three times with PBS and the color developed by adding OPD (O-phenylenediamine, Sigma Aldrich, USA) and $H_2O_2$. The readings were taken 10 min after the addition of 1N sulfuric acid. Antibody titer as a measure of seroconversion in animals was estimated as the reciprocal of the serum dilution that is above that of control animal+3× standard deviation of the control value. Antibody titers to HbsAg were estimated using the Axsym Ausab kit (Abbot Laboratories) as per the kit protocol provided by the manufacturer. A titer of 10 mIU/mL was considered as the cut-off for seroconversion. The antibody concentrations were expressed as mIU/mL. Diptheria antitoxins were estimated by the toxin neutralization test (TNT) in guinea pigs. Six animals were used per test group, control group and for the reference standard group. The reference standards were obtained from NIBSC. The dilutions of the vaccine and the reference standard were injected subcutaneously into the guinea pig and the control group received equal volume of the vehicle containing aluminum hydroxide. After four weeks the vaccinated animals were challenged with 100 LD50 of the diphtheria toxin. The control group was challenged with 1 LD50 of the toxin. The animals were observed for mortality in the different dilution groups and scored against the reference standard group. The cut off for potency was 30 IU/dose. All the animals seroconverted for the diphtheria toxin. The tetanus toxoid potency was assayed in Balb/c mice. Six animals were included in each test, reference standard and the control group. Four two-fold serial dilutions of the TT were injected in a volume of 0.5 ml subcutaneously in each mouse. After four weeks the vaccinated animals (both the test vaccine and the reference standard groups) were challenged with 100 LD50 of tetanus toxin in a volume of 0.5 ml. Control group were challenged with ⅕₀ to 1/200 dilution of the tetanus toxin. The animals were observed for mortality. The potency of the results was expressed in IU/ml (Table 1). The cut off for potency is 60 IU/dose. All the animals that were concomitantly administered the vaccines seroconverted and no antigenic interference of the vaccines antigens or alum was observed. The potency of the acellular pertussis components were assayed by ELISA against the antibody titers elicited by the detoxified pertussis toxin using reference standard from NIBSC. Antibody titer against pertactin proteins were also determined

TABLE 1

Potency testing of concomitantly administered vaccine antigens

| Vaccine antigens | Animals for testing | % seroconversion | antibody titer (average of 6 animals) | Method for antibody assay |
| --- | --- | --- | --- | --- |
| HEV + HbsAg-HPVL2 (or HEV-HPVL2)@ + HPV16 L1 + HPV18 L1 + Tdap Tdap components: Tetanus Diptheria | Mice, Balb/c Mice, Balb/c Guinea pigs | 100% | Anti-HbsAg (as HbsAg-L2) = 32 mIU/ml Anti HEV = 128,000* (measures HEV antibody to both HEV and HEV-L2 antigens) | ELISA, (Axsym Ausab, Abbot Laboratories) in-house indirect ELISA |

TABLE 1-continued

Potency testing of concomitantly administered vaccine antigens

| Vaccine antigens | Animals for testing | % seroconversion | antibody titer (average of 6 animals) | Method for antibody assay |
|---|---|---|---|---|
| Acellular pertussis antigens: detoxified pertussis toxin Pertactin FHA | | | Anti-HPV16L1 = 64,000* Anti-HPV18L1 = 128,000* Anti-HPV16 L2 = 12,800* (measures L2 antibody to both HEV-L2 and/or HbsAg-L2 antigens. Tetanus antitoxin = 75 IU/ml Diptheria antitoxin = 45 IU/ml Detox pertussis antitoxin = 12800* Anti-pertactin = 6400* Anti-FHA | in-house indirect ELISA in-house indirect ELISA in-house indirect ELISA Toxin neutralization test Toxin neutralization test in-house ELISA in-house ELISA not determined |

*Antibody titer was estimated as the reciprocal of the serum dilution that is above that of control animal + 3 × standard deviation of the control value.
@administration of either of the HbsAg-L2 or HEV-L2 elicited immune response against L2 epitope without interference from other antigens.

REFERENCES

1. Emerson U E, Purcell R H. (2007): in Fields Virology, eds Knipe D, Howley P (Lippincott Williams & Wilkins, Philadelphia), Vol 1, pp 3047-3058.
2. Chandra V, Taneja S, Kalia M, Jameel S. (2008): Molecular biology and pathogenesis of hepatitis E virus. J. Biosci 33, 451-464.
3. Guu T S, Liu Z, Ye Q, Mata D A, Li K, Yin C, Zhang J, Tao Y J. (2009): Structure of the hepatitis E virus-like particle suggests mechanisms for virus assembly and receptor binding. Proc Natl Acad Sci USA. 106, 12992-12997.
4. Khuroo M S, Teli M R, Skidmore S, et al. (1981): Incidence and severity of viral hepatitis in pregnancy. Am J Med 70:252-255.
5. Tsega E, Krawzyski K, Hansson L, et al. 1993: Hepatitis E virus infection in pregnancy in Ethiopia. Ethiop Med J 1993; 31:173-181.
6. Lindemann M L M, Morales J G, Fernández-Barrado S, et al. (2010): Case report: fulminant hepatitis E in a woman taking oral contraceptive medication. Am J Trop Med Hyg, 82, 12-15.
7. Schofield F D, Tucker V M, Westbrook G R. (1961): Neonatal tetanus in New Guinea. Effect of active immunization in pregnancy. Br Med J 2, 785-789.
8. Nanda S. K, Yalcinkaya K, Panigrahi A. K, Acharya S. K, Jameel S and Panda S. K. (1994): "Etiological role of hepatitis E virus in sporadic fulminant hepatitis," Journal of Medical Virology, 42, 133-137.
9. Beniwal M, Kumar A, Kar P, (2003): Prevalence and severity of acute viral hepatitis and fulminant hepatitis during pregnancy: a prospective study from North India. Indian J Med Microbiol. 21, 184-185.
10. Kumar A, Beniwal B, Kar P, et al. (2004): Hepatitis E in pregnancy. Int J Gynaecol Obstet. 85, 240-244.
11. Khuroo M S, Salimi K, Jameel S. (1995): Vertical transmission of hepatitis E virus. Lancet. 345, 1025-1026.
12. Amini-Bavil-Olyaee S, Trautwein C, Tacke F. (2009): Hepatitis E Vaccine: Current Status and Future Prospects. Future Virology. 4, 143-154.
13. Zhu et al., (2010): Efficacy and safety of a recombinant hepatitis E vaccine in healthy adults: a large-scale, randomised, double-blind placebo-controlled, phase 3 trial. The Lancet, 376, 895-902.
14. Mushahwar I K. (2008): Hepatitis E virus: molecular virology, clinical features, diagnosis, transmission, epidemiology, and prevention. J Med Virol. 80, 646-658.

We claim:

1. A combination vaccine composition comprising:

(i) a diphtheria toxoid, D';

(ii) a tetanus toxoid, 'T';

(iii) pertussis antigens 'aP';

(iv) recombinant human papillomavirus L1 antigens of HPV16 and HPV18; and (v) a chimeric fusion protein comprising an HPV L2 epitope in fusion with Hepatitis E ORF2 (HEV ORF2) protein wherein the chimeric fusion protein is expressed as virus like particles.

2. The combination vaccine composition according to claim 1, wherein the HPV L2 epitope is fused at the N-terminus of HEV ORF2 protein.

3. The combination vaccine composition according to claim 2, wherein the amino acid sequence of the chimeric fusion protein is set forth in SEQ ID NO: 6 or SEQ ID NO: 10.

4. The combination vaccine composition according to claim 2, wherein the nucleotide sequence encoding the chimeric fusion protein is set forth in SEQ ID NO: 5 or SEQ ID NO: 9.

5. The combination vaccine composition according to claim 1, wherein the HPV L2 epitope is fused at the C-terminus end of HEV ORF2 protein.

6. The combination vaccine composition according to claim 5, wherein the amino acid sequence of the chimeric fusion protein is set forth in SEQ ID NO: 8 or SEQ ID NO: 12.

7. The combination vaccine composition according to claim 5, wherein the nucleotide sequence encoding the chimeric fusion protein is set forth in SEQ ID NO: 7 or SEQ ID NO: 11.

8. The combination vaccine composition according to claim 1, wherein the chimeric fusion protein comprises SEQ ID NO: 6, wherein SEQ ID NO: 6 is encoded by SEQ ID NO: 5 that is codon optimized for enhanced expression as a virus like particle in *Pichia pastoris*.

9. The combination vaccine composition according to claim 1, wherein the chimeric fusion protein comprises SEQ ID NO: 8, wherein SEQ ID NO: 8 is encoded by SEQ ID NO: 7 that is codon optimized for enhanced expression as a virus like particle in *Pichia pastoris*.

10. The combination vaccine composition according to claim 1, wherein the chimeric fusion protein comprises SEQ ID NO: 10, wherein SEQ ID NO: 10 is encoded by SEQ ID NO: 9 that is codon optimized for enhanced expression as a virus like particle in *Pichia pastoris*.

11. The combination vaccine composition according to claim 1, wherein the chimeric fusion protein comprises SEQ ID NO: 12, wherein SEQ ID NO: 12 is encoded by SEQ ID NO: 11 that is codon optimized for enhanced expression as a virus like particle in *Pichia pastoris*.

12. The combination vaccine composition according to claim 1, wherein the recombinant antigens are cloned, expressed and purified from yeast cells *Pichia pastoris*.

13. The combination vaccine composition according to claim 1, further comprising an adjuvant.

14. The combination vaccine composition according to claim 13, wherein the adjuvant is alum, selected from aluminum hydroxide or aluminum phosphate, and gamma inulin and algammulin.

15. A kit comprising the combination vaccine composition according to claim 1.

16. A kit comprising the combination vaccine composition according to claim 1, wherein DTaP is formulated in aluminum hydroxide.

17. A kit comprising the combination vaccine composition according to claim 1, wherein, the kit comprises:

(a) a first component comprising HEV, HPV and chimeric HEV or HBsAg antigens; and (b) a second component comprising DTaP;

wherein contents of the first component and the second component are mixed prior to administration.

18. The combination vaccine according to claim 1, further comprising a recombinant HEV ORF 2 antigen.

* * * * *

SEQUENCE LISTING

<160> NUMBER OF SEQ ID NOS: 23

<210> SEQ ID NO 1
<211> LENGTH: 660
<212> TYPE: PRT
<213> ORGANISM: Artificial Sequence
<220> FEATURE:
<223> OTHER INFORMATION: HEV ORF2

<400> SEQUENCE: 1

Met Arg Pro Arg Pro Ile Leu Leu Leu Phe Leu Met Phe Leu Pro Met
1               5                   10                  15

Leu Pro Ala Pro Pro Gly Gln Pro Ser Gly Arg Arg Arg Gly Arg
            20                  25                  30

Arg Ser Gly Gly Ser Gly Gly Phe Trp Gly Asp Arg Val Asp Ser
         35              40              45

Gln Pro Phe Ala Ile Pro Tyr Ile His Pro Thr Asn Pro Phe Ala Pro
 50              55              60

Asp Val Thr Ala Ala Gly Ala Gly Pro Arg Val Arg Gln Pro Ala
 65              70              75              80

Arg Pro Leu Gly Ser Ala Trp Arg Asp Gln Ala Gln Arg Pro Ala Ala
                 85              90              95

Ala Ser Arg Arg Arg Pro Thr Thr Gly Ala Ala Pro Leu Thr Ala
         100             105             110

Val Ala Pro Ala His Asp Thr Pro Val Pro Asp Val Asp Ser Arg
         115             120             125

Gly Ala Ile Leu Arg Arg Gln Tyr Asn Leu Ser Thr Ser Pro Leu Thr
 130             135             140

Ser Ser Val Ala Thr Gly Thr Asn Leu Val Leu Tyr Ala Ala Pro Leu
145             150             155             160

Ser Pro Leu Leu Pro Leu Gln Asp Gly Thr Asn Thr His Ile Met Ala
                 165             170             175

Thr Glu Ala Ser Asn Tyr Ala Gln Tyr Arg Val Ala Arg Ala Thr Ile
                 180             185             190

Arg Tyr Arg Pro Leu Val Pro Asn Ala Val Gly Gly Tyr Ala Ile Ser
         195             200             205

Ile Ser Phe Trp Pro Gln Thr Thr Thr Pro Thr Ser Val Asp Met
210             215             220

Asn Ser Ile Thr Ser Thr Asp Val Arg Ile Leu Val Gln Pro Gly Ile
225             230             235             240

Ala Ser Glu Leu Val Ile Pro Ser Glu Arg Leu His Tyr Arg Asn Gln
                 245             250             255

Gly Trp Arg Ser Val Glu Thr Ser Gly Val Ala Glu Glu Ala Thr
         260             265             270

Ser Gly Leu Val Met Leu Cys Ile His Gly Ser Pro Val Asn Ser Tyr
         275             280             285

Thr Asn Thr Pro Tyr Thr Gly Ala Leu Gly Leu Leu Asp Phe Ala Leu
 290             295             300

Glu Leu Glu Phe Arg Asn Leu Thr Pro Gly Asn Thr Asn Thr Arg Val
305             310             315             320

Ser Arg Tyr Ser Ser Thr Ala Arg His Arg Leu Arg Arg Gly Ala Asp
                 325             330             335

Gly Thr Ala Glu Leu Thr Thr Thr Ala Ala Thr Arg Phe Met Lys Asp
         340             345             350

Leu Tyr Phe Thr Ser Thr Asn Gly Val Gly Glu Ile Gly Arg Gly Ile
         355             360             365

Ala Leu Thr Leu Phe Asn Leu Ala Asp Thr Leu Leu Gly Gly Leu Pro
         370             375             380

Thr Glu Leu Ile Ser Ser Ala Gly Gly Gln Leu Phe Tyr Ser Arg Pro
385             390             395             400

Val Val Ser Ala Asn Gly Glu Pro Thr Val Lys Leu Tyr Thr Ser Val
                 405             410             415

Glu Asn Ala Gln Gln Asp Lys Gly Ile Ala Ile Pro His Asp Ile Asp
         420             425             430

Leu Gly Glu Ser Arg Val Val Ile Gln Asp Tyr Asp Asn Gln His Glu
         435             440             445

Gln Asp Arg Pro Thr Pro Ser Pro Ala Pro Ser Arg Pro Phe Ser Val

```
            450                 455                 460
Leu Arg Ala Asn Asp Val Leu Trp Leu Ser Leu Thr Ala Ala Glu Tyr
465                 470                 475                 480

Asp Gln Ser Thr Tyr Gly Ser Ser Thr Gly Pro Val Tyr Val Ser Asp
                485                 490                 495

Ser Val Thr Leu Val Asn Val Ala Thr Gly Ala Gln Ala Val Ala Arg
            500                 505                 510

Ser Leu Asp Trp Thr Lys Val Thr Leu Asp Gly Arg Pro Leu Ser Thr
        515                 520                 525

Ile Gln Gln Tyr Ser Lys Thr Phe Phe Val Leu Pro Leu Arg Gly Lys
    530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Leu Leu Val Glu Asn Ala Ala Gly
                565                 570                 575

His Arg Val Ala Ile Ser Thr Tyr Thr Thr Ser Leu Gly Ala Gly Pro
            580                 585                 590

Val Ser Ile Ser Ala Val Ala Val Leu Ala Pro His Ser Ala Leu Ala
        595                 600                 605

Leu Leu Glu Asp Thr Leu Asp Tyr Pro Ala Arg Ala His Thr Phe Asp
    610                 615                 620

Asp Phe Cys Pro Glu Cys Arg Pro Leu Gly Leu Gln Gly Cys Ala Phe
625                 630                 635                 640

Gln Ser Thr Val Ala Glu Leu Gln Arg Leu Lys Met Lys Val Gly Lys
                645                 650                 655

Thr Arg Glu Leu
            660

<210> SEQ ID NO 2
<211> LENGTH: 473
<212> TYPE: PRT
<213> ORGANISM: Artificial Sequence
<220> FEATURE:
<223> OTHER INFORMATION: HPV16 L2

<400> SEQUENCE: 2

Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro Asp Ile
                20                  25                  30

Ile Pro Lys Val Glu Gly Lys Thr Ile Ala Asp Gln Ile Leu Gln Tyr
            35                  40                  45

Gly Ser Met Gly Val Phe Phe Gly Gly Leu Gly Ile Gly Thr Gly Ser
        50                  55                  60

Gly Thr Gly Gly Arg Thr Gly Tyr Ile Pro Leu Gly Thr Arg Pro Pro
65                  70                  75                  80

Thr Ala Thr Asp Thr Leu Ala Pro Val Arg Pro Pro Leu Thr Val Asp
                85                  90                  95

Pro Val Gly Pro Ser Asp Pro Ser Ile Val Ser Leu Val Glu Glu Thr
            100                 105                 110

Ser Phe Ile Asp Ala Gly Ala Pro Thr Pro Val Pro Ser Ile Pro Pro
        115                 120                 125

Asp Val Ser Gly Phe Ser Ile Thr Thr Ser Thr Asp Thr Thr Pro Ala
    130                 135                 140

Ile Leu Asp Ile Asn Asn Thr Val Thr Thr Val Thr Thr His Asn Asn
```

```
                    145                 150                 155                 160
Pro Thr Phe Thr Asp Pro Ser Val Leu Gln Pro Pro Thr Pro Ala Glu
                165                 170                 175
Thr Gly Gly His Phe Thr Leu Ser Ser Ser Thr Ile Ser Thr His Asn
            180                 185                 190
Tyr Glu Glu Ile Pro Met Asp Thr Phe Ile Val Ser Thr Asn Pro Asn
        195                 200                 205
Thr Val Thr Ser Ser Thr Pro Ile Pro Gly Ser Arg Pro Val Ala Arg
    210                 215                 220
Leu Gly Leu Tyr Ser Arg Thr Thr Gln Gln Val Lys Val Val Asp Pro
225                 230                 235                 240
Ala Phe Val Thr Thr Pro Thr Lys Leu Ile Thr Tyr Asp Asn Pro Ala
                245                 250                 255
Tyr Glu Gly Ile Asp Val Asp Asn Thr Leu Tyr Phe Ser Ser Asn Asp
            260                 265                 270
Asn Ser Ile Asn Ile Ala Pro Asp Pro Asp Phe Leu Asp Ile Val Ala
        275                 280                 285
Leu His Arg Pro Ala Leu Thr Ser Arg Arg Thr Gly Ile Arg Tyr Ser
    290                 295                 300
Arg Ile Gly Asn Lys Gln Thr Leu Arg Thr Arg Ser Gly Lys Ser Ile
305                 310                 315                 320
Gly Ala Lys Val His Tyr Tyr Tyr Asp Phe Ser Thr Ile Asp Pro Ala
                325                 330                 335
Glu Glu Ile Glu Leu Gln Thr Ile Thr Pro Ser Thr Tyr Thr Thr Thr
            340                 345                 350
Ser His Ala Ala Ser Pro Thr Ser Ile Asn Asn Gly Leu Tyr Asp Ile
        355                 360                 365
Tyr Ala Asp Asp Phe Ile Thr Asp Thr Ser Thr Thr Pro Val Pro Ser
    370                 375                 380
Val Pro Ser Thr Ser Leu Ser Gly Tyr Ile Pro Ala Asn Thr Thr Ile
385                 390                 395                 400
Pro Phe Gly Gly Ala Tyr Asn Ile Pro Leu Val Ser Gly Pro Asp Ile
                405                 410                 415
Pro Ile Asn Ile Thr Asp Gln Ala Pro Ser Leu Ile Pro Ile Val Pro
            420                 425                 430
Gly Ser Pro Gln Tyr Thr Ile Ile Ala Asp Ala Gly Asp Phe Tyr Leu
        435                 440                 445
His Pro Ser Tyr Tyr Met Leu Arg Lys Arg Arg Lys Arg Leu Pro Tyr
    450                 455                 460
Phe Phe Ser Asp Val Ser Leu Ala Ala
465                 470

<210> SEQ ID NO 3
<211> LENGTH: 1494
<212> TYPE: DNA
<213> ORGANISM: Artificial Sequence
<220> FEATURE:
<223> OTHER INFORMATION: HEV ORF2 DNA

<400> SEQUENCE: 3
atggccgttg cacctgctca tgatactcct ccagttccag atgttgattc tagaggtgct      60
atcttgagaa gacaatacaa ccttagtacc tctcctttga cttcttccgt tgctactggt     120
acaaatcttg tcttgtacgc agctccactt tcacctcttt tgccattgca agacggaacc     180
aacactcaca tcatggctac agaagccagt aattatgctc agtacagagt tgccagagca     240
```

-continued

```
actattagat atagaccttt ggttccaaac gcagtcggag gttacgctat ttccatctca      300
ttctggccac aaaccactac aacccctact tctgttgata tgaactctat cacatcaacc      360
gacgttagaa ttttggtcca accaggtatc gcttctgagc ttgttattcc ttccgaaaga      420
ttgcattata gaaaccaggg ttggagatcc gttgaaacat caggagtcgc agaagaggaa      480
gctacctctg gtcttgttat gttgtgtatt cacggaagtc cagtcaactc ttatactaat      540
acaccttaca ctggagcatt gggtcttttg gattttgctc ttgagttgga gtttagaaat      600
ttgactcctg gtaacaccaa cactagagtt tctagatact caagtactgc tagacataga      660
ttgagaagag gagccgatgg tactgcagag ttgactacaa ccgccgcaac aagattcatg      720
aaagacttgt acttcacatc caccaacgga gttggtgaaa ttggaagagg tatcgccctt      780
acattgttta atttggcaga tacccttttg ggaggtcttc caactgagtt gatttcttcc      840
gctggaggtc aattgttcta ttctagacca gttgtctccg ctaacggaga gcctacagtt      900
aaattgtaca cctcagtcga aaatgctcaa caggataagg gtattgccat ccctcatgat      960
atcgacttgg gagagtctag agttgtcatt caggattacg acaaccaaca cgaacaggac     1020
agacctactc catcccctgc cccatctaga ccatttttctg ttttgagagc aaatgatgtc     1080
ctttggttgt cacttactgc tgccgaatat gaccaaagta cttacggttc aagtacagga     1140
cctgtttatg tcagtgattc tgttaccttg gttaacgtcg ctactggtgc tcaggccgtt     1200
gcaagatcct tggattggac taaggtcaca cttgacggaa gaccattgtc aacaattcaa     1260
cagtacagta agacctttt cgttttgcct cttcgtggta aattgtcttt ctgggaagcc      1320
ggtactacaa aggcaggata cccatataac tacaatacca ctgcttccga tcaactttg      1380
gttgagaatg cagctggtca cagagtcgct atctcaactt atacaaccag tttgggagcc     1440
ggtccagttt ccatttcagc tgttgccgtc cttgctcctc attctgcatt ggct           1494
```

<210> SEQ ID NO 4
<211> LENGTH: 498
<212> TYPE: PRT
<213> ORGANISM: Artificial Sequence
<220> FEATURE:
<221> NAME/KEY: 112-608 AA
<223> OTHER INFORMATION: HEV ORF2

<400> SEQUENCE: 4

```
Met Ala Val Ala Pro Ala His Asp Thr Pro Val Pro Asp Val Asp
1               5                   10                  15

Ser Arg Gly Ala Ile Leu Arg Arg Gln Tyr Asn Leu Ser Thr Ser Pro
            20                  25                  30

Leu Thr Ser Ser Val Ala Thr Gly Thr Asn Leu Val Leu Tyr Ala Ala
        35                  40                  45

Pro Leu Ser Pro Leu Leu Pro Leu Gln Asp Gly Thr Asn Thr His Ile
    50                  55                  60

Met Ala Thr Glu Ala Ser Asn Tyr Ala Gln Tyr Arg Val Ala Arg Ala
65                  70                  75                  80

Thr Ile Arg Tyr Arg Pro Leu Val Pro Asn Ala Val Gly Gly Tyr Ala
                85                  90                  95

Ile Ser Ile Ser Phe Trp Pro Gln Thr Thr Thr Pro Thr Ser Val
            100                 105                 110

Asp Met Asn Ser Ile Thr Ser Thr Asp Val Arg Ile Leu Val Gln Pro
        115                 120                 125

Gly Ile Ala Ser Glu Leu Val Ile Pro Ser Glu Arg Leu His Tyr Arg
```

```
            130                 135                 140
Asn Gln Gly Trp Arg Ser Val Glu Thr Ser Gly Val Ala Glu Glu
145                 150                 155                 160

Ala Thr Ser Gly Leu Val Met Leu Cys Ile His Gly Ser Pro Val Asn
                165                 170                 175

Ser Tyr Thr Asn Thr Pro Tyr Thr Gly Ala Leu Gly Leu Leu Asp Phe
            180                 185                 190

Ala Leu Glu Leu Glu Phe Arg Asn Leu Thr Pro Gly Asn Thr Asn Thr
        195                 200                 205

Arg Val Ser Arg Tyr Ser Ser Thr Ala Arg His Arg Leu Arg Arg Gly
    210                 215                 220

Ala Asp Gly Thr Ala Glu Leu Thr Thr Thr Ala Ala Thr Arg Phe Met
225                 230                 235                 240

Lys Asp Leu Tyr Phe Thr Ser Thr Asn Gly Val Gly Glu Ile Gly Arg
                245                 250                 255

Gly Ile Ala Leu Thr Leu Phe Asn Leu Ala Asp Thr Leu Leu Gly Gly
            260                 265                 270

Leu Pro Thr Glu Leu Ile Ser Ser Ala Gly Gly Gln Leu Phe Tyr Ser
        275                 280                 285

Arg Pro Val Val Ser Ala Asn Gly Glu Pro Thr Val Lys Leu Tyr Thr
    290                 295                 300

Ser Val Glu Asn Ala Gln Gln Asp Lys Gly Ile Ala Ile Pro His Asp
305                 310                 315                 320

Ile Asp Leu Gly Glu Ser Arg Val Val Ile Gln Asp Tyr Asp Asn Gln
                325                 330                 335

His Glu Gln Asp Arg Pro Thr Pro Ser Pro Ala Pro Ser Arg Pro Phe
            340                 345                 350

Ser Val Leu Arg Ala Asn Asp Val Leu Trp Leu Ser Leu Thr Ala Ala
        355                 360                 365

Glu Tyr Asp Gln Ser Thr Tyr Gly Ser Ser Thr Gly Pro Val Tyr Val
    370                 375                 380

Ser Asp Ser Val Thr Leu Val Asn Val Ala Thr Gly Ala Gln Ala Val
385                 390                 395                 400

Ala Arg Ser Leu Asp Trp Thr Lys Val Thr Leu Asp Gly Arg Pro Leu
                405                 410                 415

Ser Thr Ile Gln Gln Tyr Ser Lys Thr Phe Phe Val Leu Pro Leu Arg
            420                 425                 430

Gly Lys Leu Ser Phe Trp Glu Ala Gly Thr Thr Lys Ala Gly Tyr Pro
        435                 440                 445

Tyr Asn Tyr Asn Thr Thr Ala Ser Asp Gln Leu Leu Val Glu Asn Ala
    450                 455                 460

Ala Gly His Arg Val Ala Ile Ser Thr Tyr Thr Thr Ser Leu Gly Ala
465                 470                 475                 480

Gly Pro Val Ser Ile Ser Ala Val Ala Val Leu Ala Pro His Ser Ala
                485                 490                 495

Leu Ala
```

<210> SEQ ID NO 5
<211> LENGTH: 1572
<212> TYPE: DNA
<213> ORGANISM: Artificial Sequence
<220> FEATURE:
<223> OTHER INFORMATION: HEV-HPV16L2 chimeric gene (1572 bp) DNA

<400> SEQUENCE: 5

```
atgtctgcaa ctcagttgta taaaacttgc aagcaagctg gtacttgccc accagacatt        60
atcccaaagg ttgaaggatc cgccgttgca cctgctcatg atactcctcc agttccagat       120
gttgattcta gaggtgctat cttgagaaga caatacaacc ttagtacctc tcctttgact       180
tcttccgttg ctactggtac aaatcttgtc ttgtacgcag ctccactttc acctcttttg       240
ccattgcaag acggaaccaa cactcacatc atggctacag aagccagtaa ttatgctcag       300
tacagagttg ccagagcaac tattagatat agacctttgg ttccaaacgc agtcggaggt       360
tacgctattt ccatctcatt ctggccacaa accactacaa cccctacttc tgttgatatg       420
aactctatca catcaaccga cgttagaatt ttggtccaac caggtatcgc ttctgagctt       480
gttattcctt ccgaaagatt gcattataga accagggtt ggagatccgt tgaaacatca       540
ggagtcgcag aagaggaagc tacctctggt cttgttatgt tgtgtattca cggaagtcca       600
gtcaactctt atactaatac ccttacact ggagcattgg gtcttttgga ttttgctctt       660
gagttggagt ttagaaattt gactcctggt aacaccaaca ctagagtttc tagatactca       720
agtactgcta gacatagatt gagaagagga gccgatggta ctgcagagtt gactacaacc       780
gccgcaacaa gattcatgaa agacttgtac ttcacatcca caacggagt tggtgaaatt       840
ggaagaggta tcgcccttac attgtttaat ttggcagata ccctttttggg aggtcttcca       900
actgagttga tttcttccgc tggaggtcaa ttgttctatt ctagaccagt tgtctccgct       960
aacggagagc tacagttaa attgtacacc tcagtcgaaa atgctcaaca ggataaggt      1020
attgccatcc tcatgatat cgacttggga gagtctagag ttgtcattca ggattacgac      1080
aaccaacacg aacaggacag acctactcca tccctgccc catctagacc attttctgtt      1140
ttgagagcaa atgatgtcct ttggttgtca cttactgctg ccgaatatga ccaaagtact      1200
tacggttcaa gtacaggacc tgtttatgtc agtgattctg ttaccttggt taacgtcgct      1260
actggtgctc aggccgttgc aagatccttg gattggacta aggtcacact tgacggaaga      1320
ccattgtcaa caattcaaca gtacagtaag accttttcg ttttgcctct tcgtggtaaa      1380
ttgtctttct gggaagccgg tactacaaag gcaggatacc catataacta caataccact      1440
gcttccgatc aacttttggt tgagaatgca gctggtcaca gagtcgctat ctcaacttat      1500
acaaccagtt ggggagccgg tccagttcc atttcagctg ttgccgtcct tgctcctcat      1560
tctgcattgg ct                                                          1572
```

<210> SEQ ID NO 6
<211> LENGTH: 524
<212> TYPE: PRT
<213> ORGANISM: Artificial Sequence
<220> FEATURE:
<223> OTHER INFORMATION: HEV-HPV16 L2 chimera (524 AA)

<400> SEQUENCE: 6

Met Ser Ala Thr Gln Leu Tyr Lys Thr Cys Lys Gln Ala Gly Thr Cys
1               5                   10                  15

Pro Pro Asp Ile Ile Pro Lys Val Glu Gly Ser Ala Val Ala Pro Ala
                20                  25                  30

His Asp Thr Pro Pro Val Pro Asp Val Asp Ser Arg Gly Ala Ile Leu
            35                  40                  45

Arg Arg Gln Tyr Asn Leu Ser Thr Ser Pro Leu Thr Ser Ser Val Ala
        50                  55                  60

Thr Gly Thr Asn Leu Val Leu Tyr Ala Ala Pro Leu Ser Pro Leu Leu
65                  70                  75                  80

```
Pro Leu Gln Asp Gly Thr Asn Thr His Ile Met Ala Thr Glu Ala Ser
                85                  90                  95

Asn Tyr Ala Gln Tyr Arg Val Ala Arg Ala Thr Ile Arg Tyr Arg Pro
            100                 105                 110

Leu Val Pro Asn Ala Val Gly Gly Tyr Ala Ile Ser Ile Ser Phe Trp
        115                 120                 125

Pro Gln Thr Thr Thr Thr Pro Thr Ser Val Asp Met Asn Ser Ile Thr
    130                 135                 140

Ser Thr Asp Val Arg Ile Leu Val Gln Pro Gly Ile Ala Ser Glu Leu
145                 150                 155                 160

Val Ile Pro Ser Glu Arg Leu His Tyr Arg Asn Gln Gly Trp Arg Ser
                165                 170                 175

Val Glu Thr Ser Gly Val Ala Glu Glu Ala Thr Ser Gly Leu Val
                180                 185                 190

Met Leu Cys Ile His Gly Ser Pro Val Asn Ser Tyr Thr Asn Thr Pro
            195                 200                 205

Tyr Thr Gly Ala Leu Gly Leu Leu Asp Phe Ala Leu Glu Leu Glu Phe
        210                 215                 220

Arg Asn Leu Thr Pro Gly Asn Thr Asn Thr Arg Val Ser Arg Tyr Ser
225                 230                 235                 240

Ser Thr Ala Arg His Arg Leu Arg Arg Gly Ala Asp Gly Thr Ala Glu
                245                 250                 255

Leu Thr Thr Thr Ala Ala Thr Arg Phe Met Lys Asp Leu Tyr Phe Thr
            260                 265                 270

Ser Thr Asn Gly Val Gly Glu Ile Gly Arg Gly Ile Ala Leu Thr Leu
        275                 280                 285

Phe Asn Leu Ala Asp Thr Leu Leu Gly Gly Leu Pro Thr Glu Leu Ile
    290                 295                 300

Ser Ser Ala Gly Gly Gln Leu Phe Tyr Ser Arg Pro Val Val Ser Ala
305                 310                 315                 320

Asn Gly Glu Pro Thr Val Lys Leu Tyr Thr Ser Val Glu Asn Ala Gln
                325                 330                 335

Gln Asp Lys Gly Ile Ala Ile Pro His Asp Ile Asp Leu Gly Glu Ser
            340                 345                 350

Arg Val Val Ile Gln Asp Tyr Asp Asn Gln His Glu Gln Asp Arg Pro
        355                 360                 365

Thr Pro Ser Pro Ala Pro Ser Arg Pro Phe Ser Val Leu Arg Ala Asn
    370                 375                 380

Asp Val Leu Trp Leu Ser Leu Thr Ala Ala Glu Tyr Asp Gln Ser Thr
385                 390                 395                 400

Tyr Gly Ser Ser Thr Gly Pro Val Tyr Val Ser Asp Ser Val Thr Leu
                405                 410                 415

Val Asn Val Ala Thr Gly Ala Gln Ala Val Ala Arg Ser Leu Asp Trp
            420                 425                 430

Thr Lys Val Thr Leu Asp Gly Arg Pro Leu Ser Thr Ile Gln Gln Tyr
        435                 440                 445

Ser Lys Thr Phe Phe Val Leu Pro Leu Arg Gly Lys Leu Ser Phe Trp
    450                 455                 460

Glu Ala Gly Thr Thr Lys Ala Gly Tyr Pro Tyr Asn Tyr Asn Thr Thr
465                 470                 475                 480

Ala Ser Asp Gln Leu Leu Val Glu Asn Ala Ala Gly His Arg Val Ala
                485                 490                 495
```

Ile Ser Thr Tyr Thr Thr Ser Leu Gly Ala Gly Pro Val Ser Ile Ser
                500                 505                 510

Ala Val Ala Val Leu Ala Pro His Ser Ala Leu Ala
        515                 520

<210> SEQ ID NO 7
<211> LENGTH: 1572
<212> TYPE: DNA
<213> ORGANISM: Artificial Sequence
<220> FEATURE:
<223> OTHER INFORMATION: HEV-HPV16L2 chimeric gene (1572 bp)

<400> SEQUENCE: 7

```
atggccgttg cacctgctca tgatactcct ccagttccag atgttgattc tagaggtgct      60
atcttgagaa gacaatacaa ccttagtacc tctcctttga cttcttccgt tgctactggt     120
acaaatcttg tcttgtacgc agctccactt tcacctcttt tgccattgca agacggaacc     180
aacactcaca tcatggctac agaagccagt aattatgctc agtacagagt tgccagagca     240
actattagat atagaccttt ggttccaaac gcagtcggag ttacgctat ttccatctca      300
ttctggccac aaaccactac aaccccctact tctgttgata tgaactctat cacatcaacc    360
gacgttagaa ttttggtcca accaggtatc gcttctgagc ttgttattcc ttccgaagga    420
ttgcattata gaaaccaggg ttggagatcc gttgaaacat caggagtcgc agaagaggaa    480
gctacctctg tcttgttat gttgtgtatt acggaagtc cagtcaactc ttatactaat      540
acaccttaca ctggagcatt gggtcttttg gattttgctc ttgagttgga gtttagaaat    600
ttgactcctg gtaacaccaa cactagagtt tctagatact caagtactgc tagacataga    660
ttgagaagag gagccgatgg tactgcagag ttgactacaa ccgccgcaac aagattcatg    720
aaagacttgt acttcacatc caccaacgga gttggtgaaa ttggaagagg tatcgccctt    780
acattgttta atttggcaga tacccttttg ggaggtcttc caactgagtt gatttcttcc    840
gctgaggtc aattgttcta ttctagacca gttgtctccg ctaacggaga gcctacagtt    900
aaattgtaca cctcagtcga aaatgctcaa caggataagg gtattgccat ccctcatgat    960
atcgacttgg gagagtctag agttgtcatt caggattacg acaaccaaca cgaacaggac   1020
agacctactc catcccctgc cccatctaga ccattttctg ttttgagagc aaatgatgtc   1080
ctttggttgt cacttactgc tgccgaatat gaccaaagta cttacggttc aagtacagga   1140
cctgtttatg tcagtgattc tgttaccttg gttaacgtcg ctactggtgc tcaggccgtt   1200
gcaagatcct ggattggac taaggtcaca cttgacggaa gaccattgtc aacaattcaa   1260
cagtacagta gaccttttt cgttttgcct cttcgtggta aattgtcttt ctgggaagcc   1320
ggtactacaa aggcaggata cccatataac tacaatacca ctgcttccga tcaacttttg   1380
gttgagaatg cagctggtca cagtcgctc atctcaactt atacaaccag tttgggagcc   1440
ggtccagttt ccatttcagc tgttgccgtc cttgctcctc attctgcatt ggctggatct   1500
gcaactcagt tgtataaaac ttgcaagcaa gctggtactt gcccaccaga cattatccca   1560
aaggttgaag ga                                                       1572
```

<210> SEQ ID NO 8
<211> LENGTH: 524
<212> TYPE: PRT
<213> ORGANISM: Artificial Sequence
<220> FEATURE:
<223> OTHER INFORMATION: HEV-HPV16L2 chimeric protein (524

```
Met Ala Val Ala Pro Ala His Asp Thr Pro Val Pro Asp Val Asp
1               5                   10                  15

Ser Arg Gly Ala Ile Leu Arg Arg Gln Tyr Asn Leu Ser Thr Ser Pro
            20                  25                  30

Leu Thr Ser Ser Val Ala Thr Gly Thr Asn Leu Val Leu Tyr Ala Ala
        35                  40                  45

Pro Leu Ser Pro Leu Leu Pro Leu Gln Asp Gly Thr Asn Thr His Ile
    50                  55                  60

Met Ala Thr Glu Ala Ser Asn Tyr Ala Gln Tyr Arg Val Ala Arg Ala
65                  70                  75                  80

Thr Ile Arg Tyr Arg Pro Leu Val Pro Asn Ala Val Gly Gly Tyr Ala
                85                  90                  95

Ile Ser Ile Ser Phe Trp Pro Gln Thr Thr Thr Pro Thr Ser Val
                100                 105                 110

Asp Met Asn Ser Ile Thr Ser Thr Asp Val Arg Ile Leu Val Gln Pro
            115                 120                 125

Gly Ile Ala Ser Glu Leu Val Ile Pro Ser Glu Arg Leu His Tyr Arg
        130                 135                 140

Asn Gln Gly Trp Arg Ser Val Glu Thr Ser Gly Val Ala Glu Glu
145                 150                 155                 160

Ala Thr Ser Gly Leu Val Met Leu Cys Ile His Gly Ser Pro Val Asn
                165                 170                 175

Ser Tyr Thr Asn Thr Pro Tyr Thr Gly Ala Leu Gly Leu Leu Asp Phe
            180                 185                 190

Ala Leu Glu Leu Glu Phe Arg Asn Leu Thr Pro Gly Asn Thr Asn Thr
        195                 200                 205

Arg Val Ser Arg Tyr Ser Ser Thr Ala Arg His Arg Leu Arg Arg Gly
210                 215                 220

Ala Asp Gly Thr Ala Glu Leu Thr Thr Thr Ala Ala Thr Arg Phe Met
225                 230                 235                 240

Lys Asp Leu Tyr Phe Thr Ser Thr Asn Gly Val Gly Glu Ile Gly Arg
                245                 250                 255

Gly Ile Ala Leu Thr Leu Phe Asn Leu Ala Asp Thr Leu Leu Gly Gly
            260                 265                 270

Leu Pro Thr Glu Leu Ile Ser Ser Ala Gly Gly Gln Leu Phe Tyr Ser
    275                 280                 285

Arg Pro Val Val Ser Ala Asn Gly Glu Pro Thr Val Lys Leu Tyr Thr
    290                 295                 300

Ser Val Glu Asn Ala Gln Gln Asp Lys Gly Ile Ala Ile Pro His Asp
305                 310                 315                 320

Ile Asp Leu Gly Glu Ser Arg Val Val Ile Gln Asp Tyr Asp Asn Gln
                325                 330                 335

His Glu Gln Asp Arg Pro Thr Pro Ser Pro Ala Pro Ser Arg Pro Phe
            340                 345                 350

Ser Val Leu Arg Ala Asn Asp Val Leu Trp Leu Ser Leu Thr Ala Ala
        355                 360                 365

Glu Tyr Asp Gln Ser Thr Tyr Gly Ser Ser Thr Gly Pro Val Tyr Val
    370                 375                 380

Ser Asp Ser Val Thr Leu Val Asn Val Ala Thr Gly Ala Gln Ala Val
385                 390                 395                 400

Ala Arg Ser Leu Asp Trp Thr Lys Val Thr Leu Asp Gly Arg Pro Leu
                405                 410                 415
```

```
Ser Thr Ile Gln Gln Tyr Ser Lys Thr Phe Phe Val Leu Pro Leu Arg
                420                 425                 430
Gly Lys Leu Ser Phe Trp Glu Ala Gly Thr Thr Lys Ala Gly Tyr Pro
            435                 440                 445
Tyr Asn Tyr Asn Thr Thr Ala Ser Asp Gln Leu Leu Val Glu Asn Ala
        450                 455                 460
Ala Gly His Arg Val Ala Ile Ser Thr Tyr Thr Thr Ser Leu Gly Ala
465                 470                 475                 480
Gly Pro Val Ser Ile Ser Ala Val Ala Val Leu Ala Pro His Ser Ala
                485                 490                 495
Leu Ala Gly Ser Ala Thr Gln Leu Tyr Lys Thr Cys Lys Gln Ala Gly
            500                 505                 510
Thr Cys Pro Pro Asp Ile Ile Pro Lys Val Glu Gly
        515                 520
```

<210> SEQ ID NO 9
<211> LENGTH: 1539
<212> TYPE: DNA
<213> ORGANISM: Artificial Sequence
<220> FEATURE:
<223> OTHER INFORMATION: HEV-HPV16L2 chimeric gene (1539 bp)

<400> SEQUENCE: 9

| | | |
|---|---|---|
| atggccgttg cacctgctca tgatactcct ccagttccag atgttgattc tagaggtgct | 60 |
| atcttgagaa gacaatacaa ccttagtacc tctcctttga cttcttccgt tgctactggt | 120 |
| acaaatcttg tcttgtacgc agctccactt tcacctcttt tgccattgca agacggaacc | 180 |
| aacactcaca tcatggctac agaagccagt aattatgctc agtacagagt tgccagagca | 240 |
| actattagat atagaccttt ggttccaaac gcagtcggag gttacgctat ttccatctca | 300 |
| ttctggccac aaaccactac aaccccctact tctgttgata tgaactctat cacatcaacc | 360 |
| gacgttagaa ttttggtcca accaggtatc gcttctgagc ttgttattcc ttccgaaaga | 420 |
| ttgcattata gaaaccaggg ttggagatcc gttgaaacat caggagtcgc agaagaggaa | 480 |
| gctacctctg tcttgttat gttgtgtatt cacggaagtc cagtcaactc ttatactaat | 540 |
| acaccttaca ctggagcatt gggtcttttg gattttgctc ttgagttgga gtttagaaat | 600 |
| ttgactcctg gtaacaccaa cactagagtt tctagatact caagtactgc tagacataga | 660 |
| ttgagaagag gagccgatgg tactgcagag ttgactacaa ccgccgcaac aagattcatg | 720 |
| aaagacttgt acttcacatc caccaacgga gttggtgaaa ttggaagagg tatcgcccct | 780 |
| acattgttta atttggcaga taccctttg ggaggtcttc caactgagtt gatttcttcc | 840 |
| gctggaggtc aattgttcta ttctagacca gttgtctccg ctaacggaga gcctacagtt | 900 |
| aaattgtaca cctcagtcga aaatgctcaa caggataagg gtattgccat ccctcatgat | 960 |
| atcgacttgg gagagtctag agttgtcatt caggattacg acaaccaaca cgaacaggac | 1020 |
| agacctactc catcccctgc ccatctaga ccattttctg ttttgagagc aaatgatgtc | 1080 |
| ctttggttgt cacttactgc tgccgaatat gaccaaagta cttacggttc aagtacagga | 1140 |
| cctgtttatg tcagtgattc tgttaccttg gttaacgtcg ctactggtgc tcaggccgtt | 1200 |
| gcaagatcct ggattggac taaggtcaca cttgacggaa gaccattgtc aacaattcaa | 1260 |
| cagtacagta agacctttt cgttttgcct cttcgtggta aattgtcttt ctgggaagcc | 1320 |
| ggtactacaa aggcaggata cccatataac tacaatacca ctgcttccga tcaacttttg | 1380 |
| gttgagaatg cagctggtca cagagtcgct atctcaactt atacaaccag tttgggagcc | 1440 |

```
ggtccagttt ccatttcagc tgttgccgtc cttgctcctc attctgcatt ggctggatcc    1500
ttggttgaag aaacctcctt tattgacgct ggtgctcca                           1539
```

<210> SEQ ID NO 10
<211> LENGTH: 513
<212> TYPE: PRT
<213> ORGANISM: Artificial Sequence
<220> FEATURE:
<223> OTHER INFORMATION: HEV-HPV16L2 chimeric protein (513 AA)

<400> SEQUENCE: 10

```
Met Ala Val Ala Pro Ala His Asp Thr Pro Val Pro Asp Val Asp
1               5                   10                  15

Ser Arg Gly Ala Ile Leu Arg Arg Gln Tyr Asn Leu Ser Thr Ser Pro
            20                  25                  30

Leu Thr Ser Ser Val Ala Thr Gly Thr Asn Leu Val Leu Tyr Ala Ala
        35                  40                  45

Pro Leu Ser Pro Leu Leu Pro Leu Gln Asp Gly Thr Asn Thr His Ile
    50                  55                  60

Met Ala Thr Glu Ala Ser Asn Tyr Ala Gln Tyr Arg Val Ala Arg Ala
65                  70                  75                  80

Thr Ile Arg Tyr Arg Pro Leu Val Pro Asn Ala Val Gly Gly Tyr Ala
                85                  90                  95

Ile Ser Ile Ser Phe Trp Pro Gln Thr Thr Thr Thr Pro Thr Ser Val
            100                 105                 110

Asp Met Asn Ser Ile Thr Ser Thr Asp Val Arg Ile Leu Val Gln Pro
        115                 120                 125

Gly Ile Ala Ser Glu Leu Val Ile Pro Ser Glu Arg Leu His Tyr Arg
    130                 135                 140

Asn Gln Gly Trp Arg Ser Val Glu Thr Ser Gly Val Ala Glu Glu Glu
145                 150                 155                 160

Ala Thr Ser Gly Leu Val Met Leu Cys Ile His Gly Ser Pro Val Asn
                165                 170                 175

Ser Tyr Thr Asn Thr Pro Tyr Thr Gly Ala Leu Gly Leu Leu Asp Phe
            180                 185                 190

Ala Leu Glu Leu Glu Phe Arg Asn Leu Thr Pro Gly Asn Thr Asn Thr
        195                 200                 205

Arg Val Ser Arg Tyr Ser Ser Thr Ala Arg His Arg Leu Arg Arg Gly
    210                 215                 220

Ala Asp Gly Thr Ala Glu Leu Thr Thr Thr Ala Ala Thr Arg Phe Met
225                 230                 235                 240

Lys Asp Leu Tyr Phe Thr Ser Thr Asn Gly Val Gly Glu Ile Gly Arg
                245                 250                 255

Gly Ile Ala Leu Thr Leu Phe Asn Leu Ala Asp Thr Leu Leu Gly Gly
            260                 265                 270

Leu Pro Thr Glu Leu Ile Ser Ser Ala Gly Gly Gln Leu Phe Tyr Ser
        275                 280                 285

Arg Pro Val Val Ser Ala Asn Gly Glu Pro Thr Val Lys Leu Tyr Thr
    290                 295                 300

Ser Val Glu Asn Ala Gln Gln Asp Lys Gly Ile Ala Ile Pro His Asp
305                 310                 315                 320

Ile Asp Leu Gly Glu Ser Arg Val Val Ile Gln Asp Tyr Asp Asn Gln
                325                 330                 335

His Glu Gln Asp Arg Pro Thr Pro Ser Pro Ala Pro Ser Arg Pro Phe
            340                 345                 350
```

```
Ser Val Leu Arg Ala Asn Asp Val Leu Trp Leu Ser Leu Thr Ala Ala
        355                 360                 365

Glu Tyr Asp Gln Ser Thr Tyr Gly Ser Ser Thr Gly Pro Val Tyr Val
370                 375                 380

Ser Asp Ser Val Thr Leu Val Asn Val Ala Thr Gly Ala Gln Ala Val
385                 390                 395                 400

Ala Arg Ser Leu Asp Trp Thr Lys Val Thr Leu Asp Gly Arg Pro Leu
                405                 410                 415

Ser Thr Ile Gln Gln Tyr Ser Lys Thr Phe Phe Val Leu Pro Leu Arg
            420                 425                 430

Gly Lys Leu Ser Phe Trp Glu Ala Gly Thr Thr Lys Ala Gly Tyr Pro
        435                 440                 445

Tyr Asn Tyr Asn Thr Thr Ala Ser Asp Gln Leu Leu Val Glu Asn Ala
    450                 455                 460

Ala Gly His Arg Val Ala Ile Ser Thr Tyr Thr Thr Ser Leu Gly Ala
465                 470                 475                 480

Gly Pro Val Ser Ile Ser Ala Val Ala Val Leu Ala Pro His Ser Ala
                485                 490                 495

Leu Ala Gly Ser Leu Val Glu Glu Thr Ser Phe Ile Asp Ala Gly Ala
            500                 505                 510

Pro
```

<210> SEQ ID NO 11
<211> LENGTH: 1617
<212> TYPE: DNA
<213> ORGANISM: Artificial Sequence
<220> FEATURE:
<223> OTHER INFORMATION: HEV-HPV16 L2 chimeric gene (1617 bp)

<400> SEQUENCE: 11

```
atgtctgcaa ctcagttgta taaaacttgc aagcaagctg gtacttgccc accagacatt        60
atcccaaagg ttgaaggatc cgccgttgca cctgctcatg atactcctcc agttccagat       120
gttgattcta gaggtgctat cttgagaaga caatacaacc ttagtacctc tcctttgact       180
tcttccgttg ctactggtac aaatcttgtc ttgtacgcag ctccactttc acctcttttg       240
ccattgcaag acggaaccaa cactcacatc atggctacag aagccagtaa ttatgctcag       300
tacagagttg ccagagcaac tattagatat agacctttgg ttccaaacgc agtcggaggt       360
tacgctattt ccatctcatt ctggccacaa accactacaa cccctacttc tgttgatatg       420
aactctatca catcaaccga cgttagaatt ttggtccaac aggtatcgc ttctgagctt       480
gttattcctt ccgaaagatt gcattataga aaccagggtt ggagatccgt tgaaacatca       540
ggagtcgcag aagaggaagc tacctctggt cttgttatgt tgtgtattca cggaagtcca       600
gtcaactctt atactaatac accttacact ggagcattgg gtcttttgga ttttgctctt       660
gagttggagt ttagaaattt gactcctggt aacaccaaca ctagagtttc tagatactca       720
agtactgcta acatagatt gagaagagga gccgatggta ctgcagagtt gactacaacc       780
gccgcaacaa gattcatgaa agacttgtac ttcacatcca caacggagt tggtgaaatt       840
ggaagaggta tcgcccttac attgtttaat ttggcagata cccttttggg aggtcttcca       900
actgagttga tttcttccgc tggaggtcaa ttgttctatt ctagaccagt tgtctccgct       960
aacgagagc ctagagttaa attgtacacc tcagtcgaaa atgctcaaca ggataagggt      1020
attgccatcc ctcatgatat cgacttggga gagtctagag ttgtcattca ggattacgac      1080
```

-continued

```
aaccaacacg aacaggacag acctactcca tcccctgccc catctagacc attttctgtt   1140
ttgagagcaa atgatgtcct ttggttgtca cttactgctg ccgaatatga ccaaagtact   1200
tacggttcaa gtacaggacc tgtttatgtc agtgattctg ttaccttggt taacgtcgct   1260
actggtgctc aggccgttgc aagatccttg gattggacta aggtcacact tgacggaaga   1320
ccattgtcaa caattcaaca gtacagtaag acctttttcg ttttgcctct tcgtggtaaa   1380
ttgtctttct gggaagccgg tactacaaag gcaggatacc catataacta caataccact   1440
gcttccgatc aacttttggt tgagaatgca gctggtcaca gagtcgctat ctcaacttat   1500
acaaccagtt gggagccggt ccagttttcc atttcagctg ttgccgtcct tgctcctcat   1560
tctgcattgg ctggatcctt ggttgaagaa acctcctttta ttgacgctgg tgctcca     1617
```

<210> SEQ ID NO 12
<211> LENGTH: 539
<212> TYPE: PRT
<213> ORGANISM: Artificial Sequence
<220> FEATURE:
<223> OTHER INFORMATION: HEV-HPV16 L2 chimeric protein (539 AA)

<400> SEQUENCE: 12

```
Met Ser Ala Thr Gln Leu Tyr Lys Thr Cys Lys Gln Ala Gly Thr Cys
1               5                   10                  15

Pro Pro Asp Ile Ile Pro Lys Val Glu Gly Ser Ala Val Ala Pro Ala
                20                  25                  30

His Asp Thr Pro Pro Val Pro Asp Val Asp Ser Arg Gly Ala Ile Leu
            35                  40                  45

Arg Arg Gln Tyr Asn Leu Ser Thr Ser Pro Leu Thr Ser Ser Val Ala
        50                  55                  60

Thr Gly Thr Asn Leu Val Leu Tyr Ala Ala Pro Leu Ser Pro Leu Leu
65                  70                  75                  80

Pro Leu Gln Asp Gly Thr Asn Thr His Ile Met Ala Thr Glu Ala Ser
                85                  90                  95

Asn Tyr Ala Gln Tyr Arg Val Ala Arg Ala Thr Ile Arg Tyr Arg Pro
            100                 105                 110

Leu Val Pro Asn Ala Val Gly Gly Tyr Ala Ile Ser Ile Ser Phe Trp
        115                 120                 125

Pro Gln Thr Thr Thr Thr Pro Thr Ser Val Asp Met Asn Ser Ile Thr
    130                 135                 140

Ser Thr Asp Val Arg Ile Leu Val Gln Pro Gly Ile Ala Ser Glu Leu
145                 150                 155                 160

Val Ile Pro Ser Glu Arg Leu His Tyr Arg Asn Gln Gly Trp Arg Ser
                165                 170                 175

Val Glu Thr Ser Gly Val Ala Glu Glu Ala Thr Ser Gly Leu Val
            180                 185                 190

Met Leu Cys Ile His Gly Ser Pro Val Asn Ser Tyr Thr Asn Thr Pro
        195                 200                 205

Tyr Thr Gly Ala Leu Gly Leu Leu Asp Phe Ala Leu Glu Leu Glu Phe
    210                 215                 220

Arg Asn Leu Thr Pro Gly Asn Thr Asn Thr Arg Val Ser Arg Tyr Ser
225                 230                 235                 240

Ser Thr Ala Arg His Arg Leu Arg Arg Gly Ala Asp Gly Thr Ala Glu
                245                 250                 255

Leu Thr Thr Thr Ala Ala Thr Arg Phe Met Lys Asp Leu Tyr Phe Thr
            260                 265                 270
```

-continued

```
Ser Thr Asn Gly Val Gly Glu Ile Gly Arg Gly Ile Ala Leu Thr Leu
            275                 280                 285
Phe Asn Leu Ala Asp Thr Leu Leu Gly Gly Leu Pro Thr Glu Leu Ile
    290                 295                 300
Ser Ser Ala Gly Gly Gln Leu Phe Tyr Ser Arg Pro Val Val Ser Ala
305                 310                 315                 320
Asn Gly Glu Pro Thr Val Lys Leu Tyr Thr Ser Val Glu Asn Ala Gln
                325                 330                 335
Gln Asp Lys Gly Ile Ala Ile Pro His Asp Ile Asp Leu Gly Glu Ser
            340                 345                 350
Arg Val Val Ile Gln Asp Tyr Asp Asn Gln His Glu Gln Asp Arg Pro
        355                 360                 365
Thr Pro Ser Pro Ala Pro Ser Arg Pro Phe Ser Val Leu Arg Ala Asn
    370                 375                 380
Asp Val Leu Trp Leu Ser Leu Thr Ala Ala Glu Tyr Asp Gln Ser Thr
385                 390                 395                 400
Tyr Gly Ser Ser Thr Gly Pro Val Tyr Val Ser Asp Ser Val Thr Leu
                405                 410                 415
Val Asn Val Ala Thr Gly Ala Gln Ala Val Ala Arg Ser Leu Asp Trp
            420                 425                 430
Thr Lys Val Thr Leu Asp Gly Arg Pro Leu Ser Thr Ile Gln Gln Tyr
        435                 440                 445
Ser Lys Thr Phe Phe Val Leu Pro Leu Arg Gly Lys Leu Ser Phe Trp
    450                 455                 460
Glu Ala Gly Thr Thr Lys Ala Gly Tyr Pro Tyr Asn Tyr Asn Thr Thr
465                 470                 475                 480
Ala Ser Asp Gln Leu Leu Val Glu Asn Ala Ala Gly His Arg Val Ala
                485                 490                 495
Ile Ser Thr Tyr Thr Thr Ser Leu Gly Ala Gly Pro Val Ser Ile Ser
            500                 505                 510
Ala Val Ala Val Leu Ala Pro His Ser Ala Leu Ala Gly Ser Leu Val
        515                 520                 525
Glu Glu Thr Ser Phe Ile Asp Ala Gly Ala Pro
    530                 535
```

```
<210> SEQ ID NO 13
<211> LENGTH: 40
<212> TYPE: DNA
<213> ORGANISM: Artificial Sequence
<220> FEATURE:
<223> OTHER INFORMATION: HEVFP PCR PRIMER

<400> SEQUENCE: 13
catttgaatt caccatggcc gttgcacctg ctcatgatac                40

<210> SEQ ID NO 14
<211> LENGTH: 39
<212> TYPE: DNA
<213> ORGANISM: Artificial Sequence
<220> FEATURE:
<223> OTHER INFORMATION: HEVRP PCR PRIMER

<400> SEQUENCE: 14
tatcgcggcc gctcattaag ccaatgcaga atgaggagc                 39

<210> SEQ ID NO 15
<211> LENGTH: 40
<212> TYPE: DNA
```

```
<213> ORGANISM: Artificial Sequence
<220> FEATURE:
<223> OTHER INFORMATION: L2NTFP

<400> SEQUENCE: 15
atgtcgaatt caccatggct gcaactcagt tgtataaaac         40

<210> SEQ ID NO 16
<211> LENGTH: 32
<212> TYPE: DNA
<213> ORGANISM: Artificial Sequence
<220> FEATURE:
<223> OTHER INFORMATION: L2NTRP

<400> SEQUENCE: 16
atcgaggatc cttgaacctt tgggataatg tc                 32

<210> SEQ ID NO 17
<211> LENGTH: 34
<212> TYPE: DNA
<213> ORGANISM: Artificial Sequence
<220> FEATURE:
<223> OTHER INFORMATION: L2CTFP PCR PRIMER

<400> SEQUENCE: 17
atgtcggatc ctctgcaact cagttgtata aaac               34

<210> SEQ ID NO 18
<211> LENGTH: 43
<212> TYPE: DNA
<213> ORGANISM: Artificial Sequence
<220> FEATURE:
<223> OTHER INFORMATION: L2CTRP PCR PRIMER

<400> SEQUENCE: 18
atcgagcggc cgctcattaa ccttcaacct tgggataat gtc      43

<210> SEQ ID NO 19
<211> LENGTH: 39
<212> TYPE: DNA
<213> ORGANISM: Artificial Sequence
<220> FEATURE:
<223> OTHER INFORMATION: L2CTRP1 PCR PRIMER

<400> SEQUENCE: 19
ttggttgaag aaacctcctt tattgacgct ggtgctcca          39

<210> SEQ ID NO 20
<211> LENGTH: 35
<212> TYPE: DNA
<213> ORGANISM: Artificial Sequence
<220> FEATURE:
<223> OTHER INFORMATION: HEVNTFP PCR PRIMER

<400> SEQUENCE: 20
acgtcggatc catcgcccttt acattgttta atttg             35

<210> SEQ ID NO 21
<211> LENGTH: 39
<212> TYPE: DNA
<213> ORGANISM: Artificial Sequence
<220> FEATURE:
<223> OTHER INFORMATION: HEVNTRPPCR PRIMER

<400> SEQUENCE: 21
tatcgcggcc gctcattaag ccaatgcaga atgaggagc          39
```

-continued

```
<210> SEQ ID NO 22
<211> LENGTH: 38
<212> TYPE: DNA
<213> ORGANISM: Artificial Sequence
<220> FEATURE:
<223> OTHER INFORMATION: HEVCTFP PCR PRIMER

<400> SEQUENCE: 22
agctcgaatt caccatggcc cttacattgt ttaatttg                          38

<210> SEQ ID NO 23
<211> LENGTH: 38
<212> TYPE: DNA
<213> ORGANISM: Artificial Sequence
<220> FEATURE:
<223> OTHER INFORMATION: HEVCTRP PCR PRIMER

<400> SEQUENCE: 23
actcaggatc cttatcaagc caatgcagaa tgaggagc                          38
```